(12) United States Patent
Nakajima et al.

(10) Patent No.: US 10,098,545 B2
(45) Date of Patent: Oct. 16, 2018

(54) LENS INFORMATION MANAGEMENT SYSTEM FOR SURFACE CONDITION MEASUREMENT AND ANALYSIS AND INFORMATION MANAGEMENT METHOD FOR SURFACE CONDITION MEASUREMENT AND ANALYSIS

(71) Applicant: MAXELL HOLDINGS, LTD., Oyamazaki-cho (JP)

(72) Inventors: Hiroe Nakajima, Ibaraki (JP); Masashi Yoshimura, Ibaraki (JP)

(73) Assignee: MAXELL HOLDINGS, LTD., Kyoto (JP)

( * ) Notice: Subject to any disclaimer, the term of this patent is extended or adjusted under 35 U.S.C. 154(b) by 226 days.

(21) Appl. No.: 15/031,765

(22) PCT Filed: Oct. 23, 2014

(86) PCT No.: PCT/JP2014/078183
§ 371 (c)(1),
(2) Date: Apr. 25, 2016

(87) PCT Pub. No.: WO2015/060376
PCT Pub. Date: Apr. 30, 2015

(65) Prior Publication Data
US 2016/0262624 A1 Sep. 15, 2016

(30) Foreign Application Priority Data
Oct. 23, 2013 (JP) .................................. 2013-220389

(51) Int. Cl.
*G06K 9/00* (2006.01)
*A61B 5/00* (2006.01)
*G06T 7/00* (2017.01)

(52) U.S. Cl.
CPC ............ *A61B 5/0077* (2013.01); *A61B 5/004* (2013.01); *A61B 5/441* (2013.01); *A61B 5/444* (2013.01);
(Continued)

(58) Field of Classification Search
None
See application file for complete search history.

(56) References Cited

U.S. PATENT DOCUMENTS 5,982,953 A * 11/1999 Yanagita ............... G06F 19/321
348/580
6,993,167 B1 * 1/2006 Skladnev ............. A61B 5/0059
382/128

(Continued)

FOREIGN PATENT DOCUMENTS

JP       H08-76741 A       3/1996
JP       2002-015068 A     1/2002
(Continued)

OTHER PUBLICATIONS

Jan. 20, 2015 International Search Report issued in International Patent Application No. PCT/JP2014/078183.
(Continued)

*Primary Examiner* — Tahmina Ansari
(74) *Attorney, Agent, or Firm* — Oliff PLC

(57) ABSTRACT

Provided are a system and method for surface condition measurement and analysis to effectively utilize image data photographed when a surface as an object is photographed regularly and continuously. When a surface as an object is sequentially photographed as time passes and the photographed image data is sequentially stored, the sequentially stored images are compared and the presence or absence of image regions among the images that nearly coincide with each other is determined. When there are images with image
(Continued)

regions that nearly coincide with each other, a coordinate system having one image as a reference is set, and a position of the other image in the coordinate system is determined. When an image with an undetermined position overlaps with an image with a determined position, including images photographed subsequent thereto, the position of the image is determined.

18 Claims, 16 Drawing Sheets

(52) U.S. Cl.
CPC ............ *A61B 5/7278* (2013.01); *A61B 5/742* (2013.01); *G06T 7/0016* (2013.01); *A61B 5/7425* (2013.01); *A61B 2503/12* (2013.01); *A61B 2576/02* (2013.01); *G06T 2207/30088* (2013.01)

(56) References Cited

U.S. PATENT DOCUMENTS

| | | | | |
|---|---|---|---|---|
| 7,689,016 | B2* | 3/2010 | Stoecker | G06F 19/321 382/128 |
| 7,894,651 | B2* | 2/2011 | Gutkowicz-Krusin | A61B 5/0059 382/128 |
| 8,131,029 | B2* | 3/2012 | Chhibber | G06K 9/00288 382/118 |
| 8,290,257 | B2* | 10/2012 | Demirli | A61B 5/441 382/128 |
| 9,094,615 | B2* | 7/2015 | Aman | G01S 3/7864 |
| 2004/0125996 | A1* | 7/2004 | Eddowes | A61B 5/0059 382/128 |
| 2005/0089199 | A1* | 4/2005 | Marschner | G06K 9/4661 382/118 |
| 2008/0214907 | A1* | 9/2008 | Gutkowicz-Krusin | A61B 5/0059 600/306 |

FOREIGN PATENT DOCUMENTS

| | | |
|---|---|---|
| JP | 2002-366651 A | 12/2002 |
| JP | 2004-354207 A | 12/2004 |
| JP | 2005-056165 A | 3/2005 |
| JP | 2005-084012 A | 3/2005 |
| JP | 2005-148797 A | 6/2005 |
| JP | 2010-284239 A | 12/2010 |
| WO | WO 2012/160511 A1 * | 5/2012 |

OTHER PUBLICATIONS

Jan. 20, 2015 Written Opinion issued in International Patent Application No. PCT/JP2014/078183.

* cited by examiner

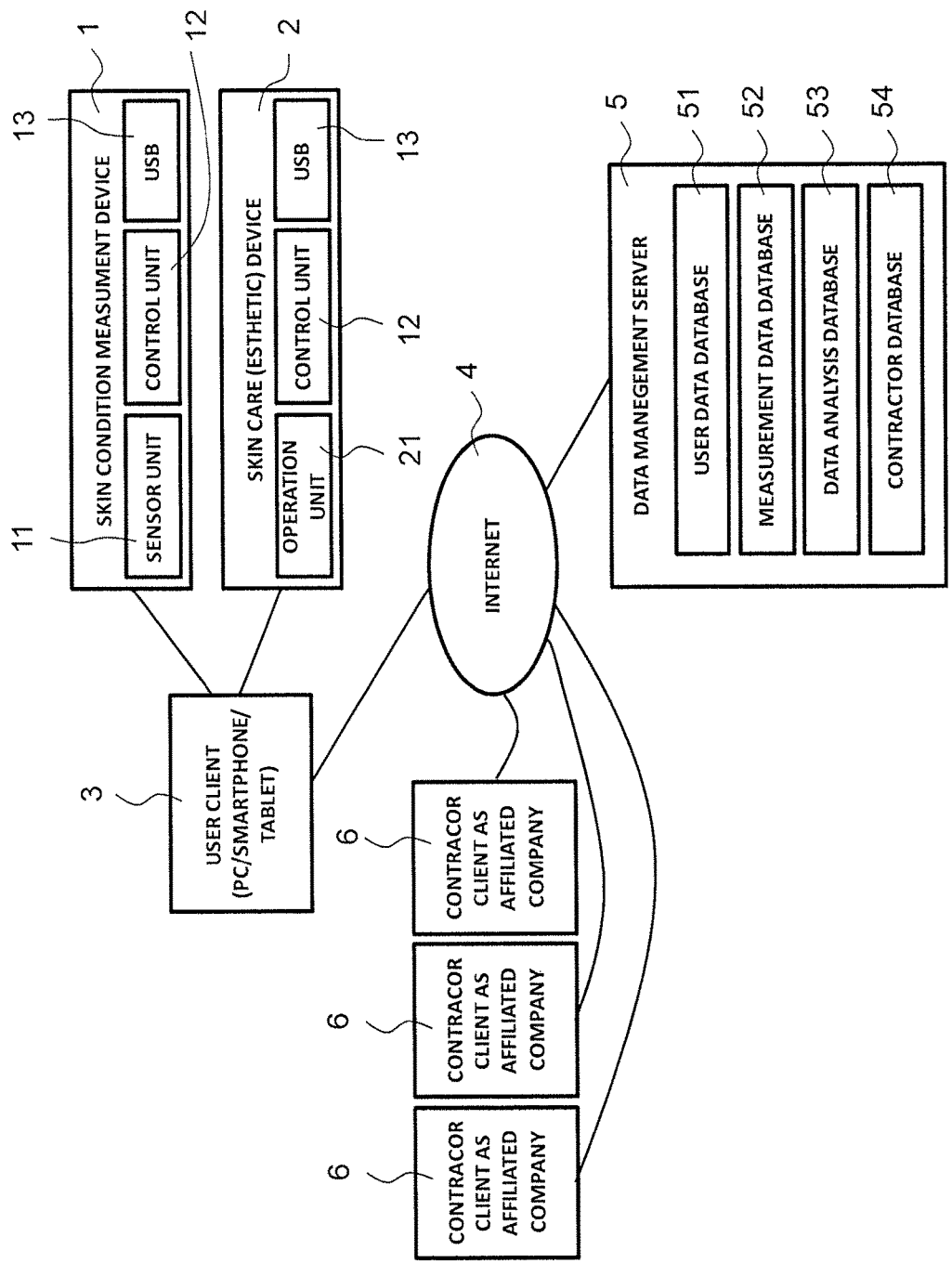
[FIG. 1]

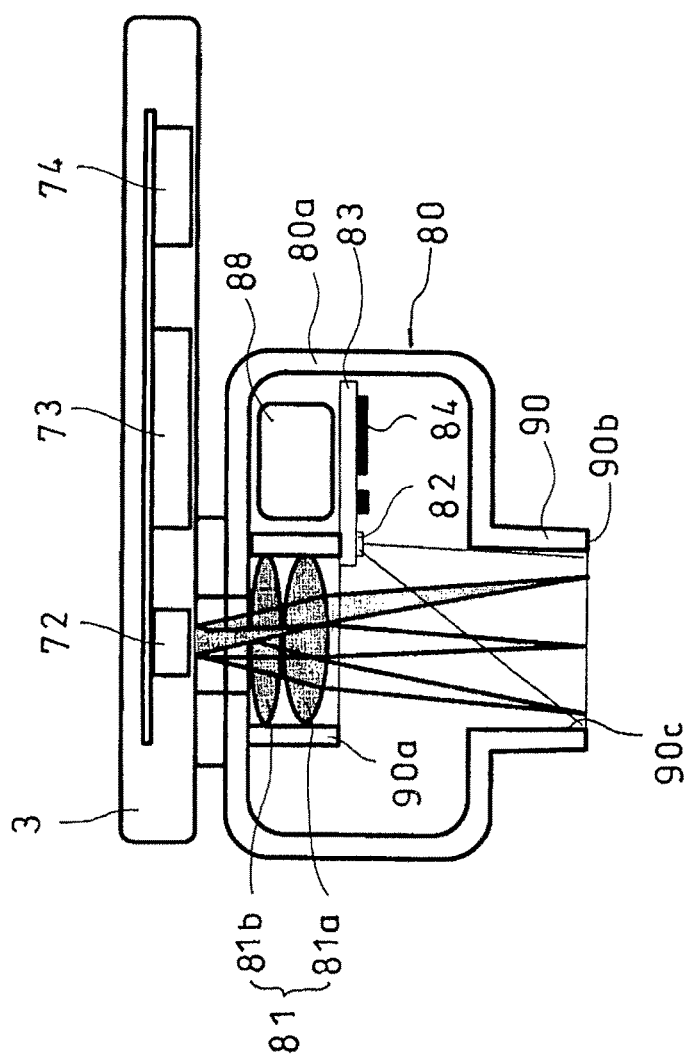
[FIG. 2]

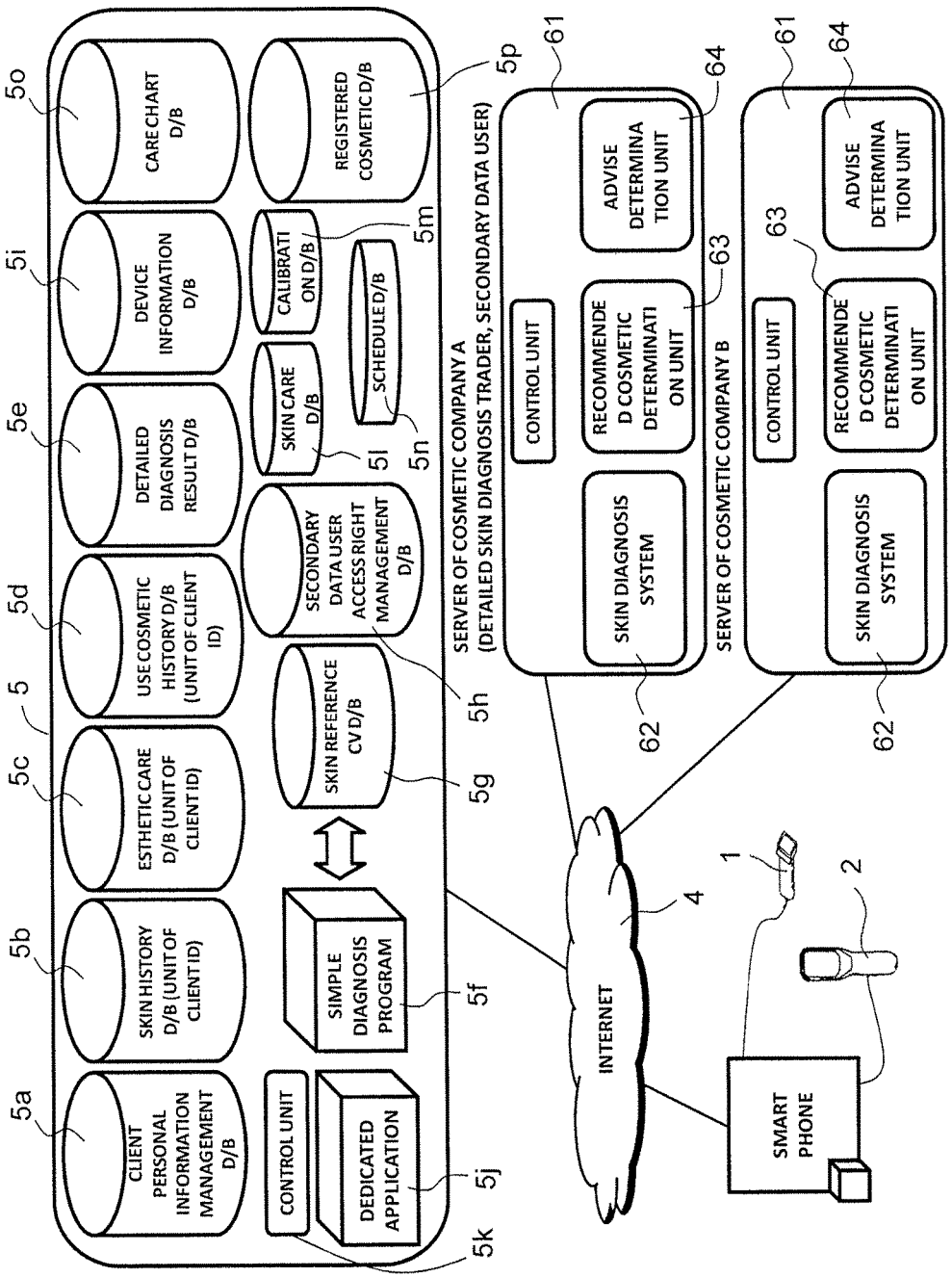
[FIG. 3]

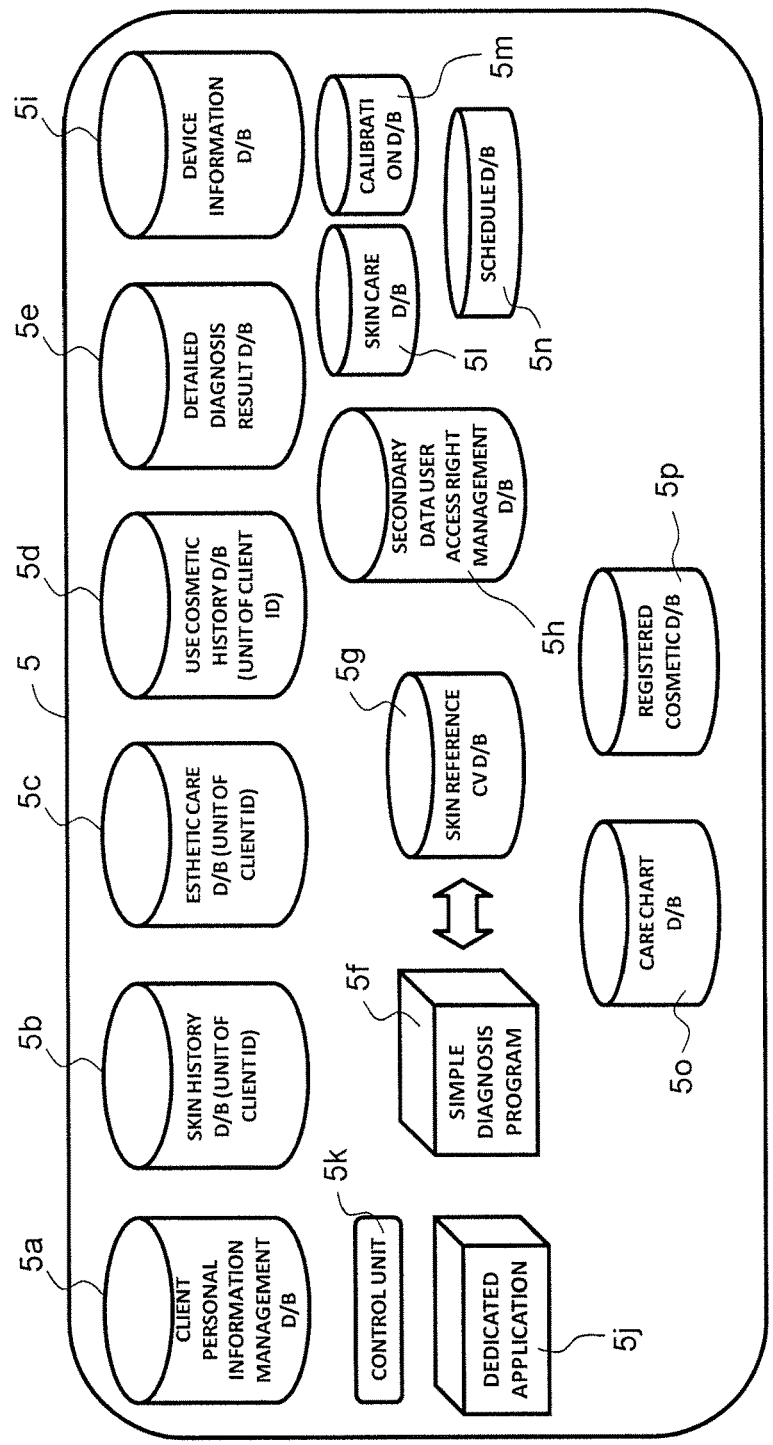
[FIG. 4]

[FIG. 5]
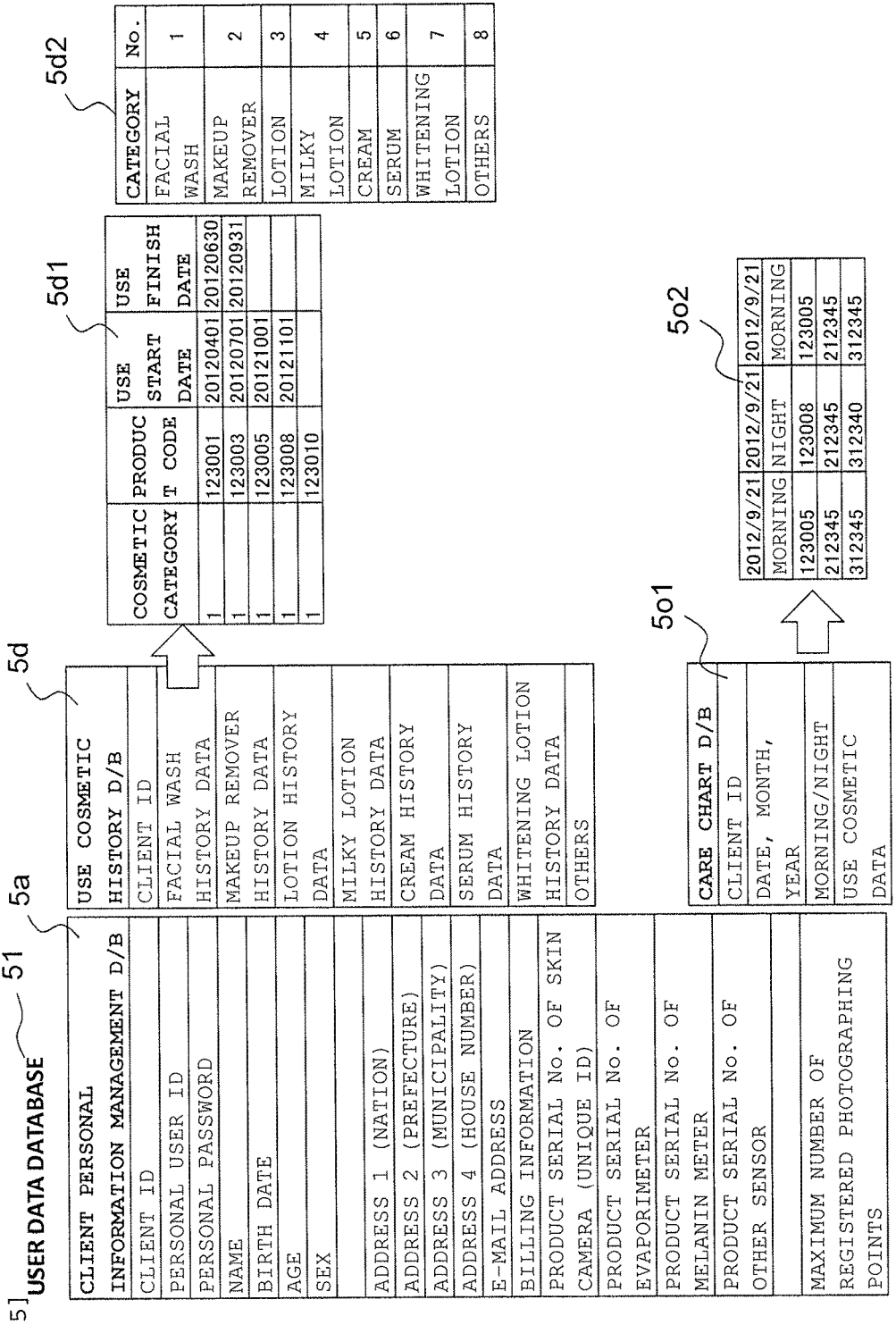

[FIG. 6]

MEASUREMENT DATA DATABASE (52)

SKIN HISTORY D/B (5b)

| SKIN HISTORY D/B |
|---|
| CLIENT ID |
| DATA NO. |
| DATA INPUT DATE AND TIME |
| GPS DATA (MEASUREMENT POINT) |
| METEOROLOGICAL DATA AT THE TIME OF MEASUREMENT FOR MEASUREMENT POINT (TEMPERATURE, HUMIDITY) |
| MEASUREMENT CONDITION FLAG |
| INPUT SKIN IMAGE |
| INPUT EVAPORATION METER DATA |
| INPUT MELANIN METER DATA |
| SIMPLE DIAGNOSIS RESULT OF SKIN IMAGE |
| SIMPLE DIAGNOSIS RESULT OF EVAPORATION METER DATA |
| SIMPLE DIAGNOSIS RESULT OF MELANIN METER DATA |
| RESULT OF COMPREHENSIVE SIMPLE ANALYSIS |
| DETAILED DIAGNOSIS RESULT STORAGE SPACE |

→ (5b1)

| |
|---|
| IMAGE FOR TEXTURE DIAGNOSIS |
| IMAGE QUALITY DATA OF TEXTURE |
| IMAGE FOR SPOT DIAGNOSIS |
| IMAGE QUALITY DATA OF SPOT |
| SKIN IMAGE |
| IMAGE QUALITY DATA OF SKIN |
| PHOTOGRAPHING POINT (CENTER COORDINATE) |
| POSITIONAL COORDINATE OF CENTER OF IMAGE |
| POSITION DETERMINATION FLAG |

→ (5b2)

| |
|---|
| SKIN TYPE |
| TEXTURE (SCORE, DEVIATION VALUE) |
| SPOT |
| WRINKLE |

PHOTOGRAPHING POINT D/B (5c)

| CLIENT ID | | | | |
|---|---|---|---|---|
| CENTER COORDINATE AT FIRST PHOTOGRAPHING POINT | REGISTERED NUMBER OF PHOTOGRAPHING POINTS (HERE 3) | | | |
| | NUMBER OF IMAGES AT FIRST PHOTOGRAPHING POINT | REGISTRATION DATE OF FIRST PHOTOGRAPHING POINT | REFERENCE IMAGE OF FIRST PHOTOGRAPHING POINT (DATA No.) | PORE DATA OF FIRST PHOTOGRAPHING POINT |
| CENTER COORDINATE AT SECOND PHOTOGRAPHING POINT | NUMBER OF IMAGES AT SECOND PHOTOGRAPHING POINT | REGISTRATION DATE OF SECOND PHOTOGRAPHING POINT | REFERENCE IMAGE OF SECOND PHOTOGRAPHING POINT (DATA No.) | PORE DATA OF SECOND PHOTOGRAPHING POINT |
| CENTER COORDINATE AT THIRD PHOTOGRAPHING POINT | NUMBER OF IMAGES AT THIRD PHOTOGRAPHING POINT | REGISTRATION DATE OF THIRD PHOTOGRAPHING POINT | REFERENCE IMAGE OF THIRD PHOTOGRAPHING POINT (DATA No.) | PORE DATA OF THIRD PHOTOGRAPHING POINT |

→ (5b4)

| DATA NUMBER n |
|---|
| (r1, θ1) |
| (r2, θ2) |
| (r3, θ3) |
| ... |
| (m, θn) |

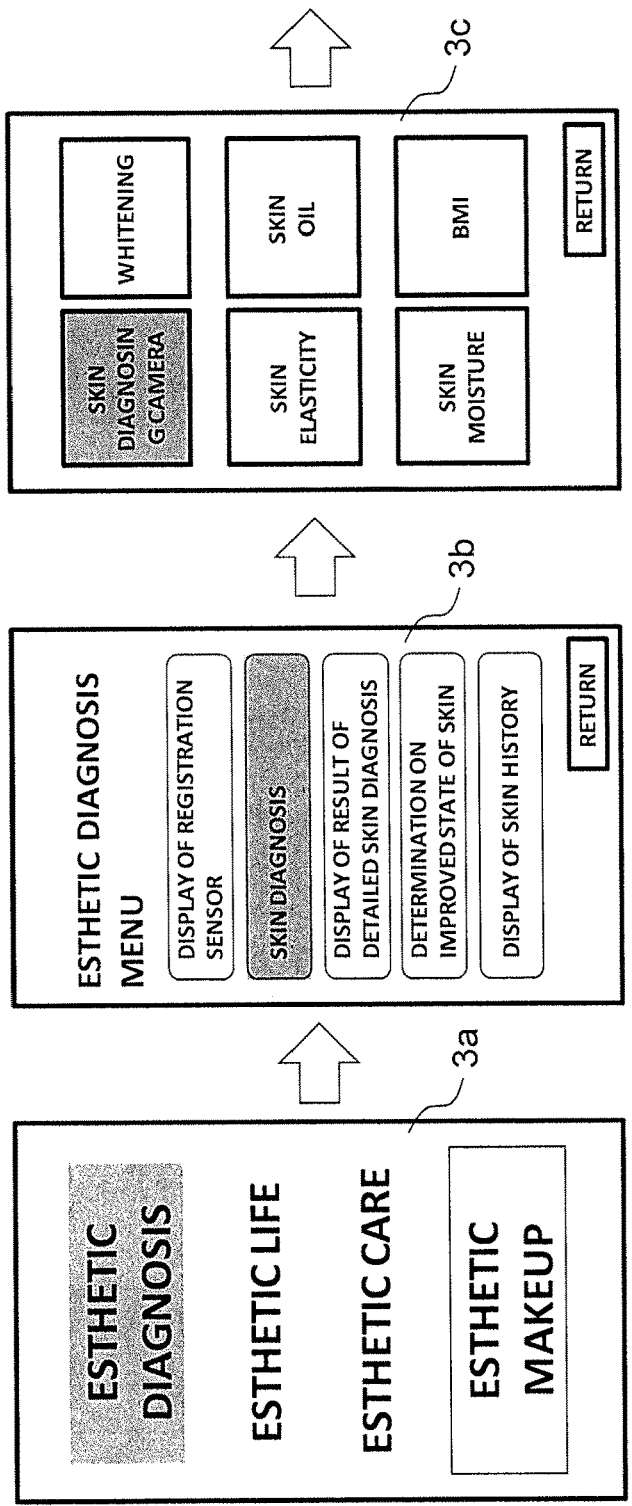
[FIG. 7]

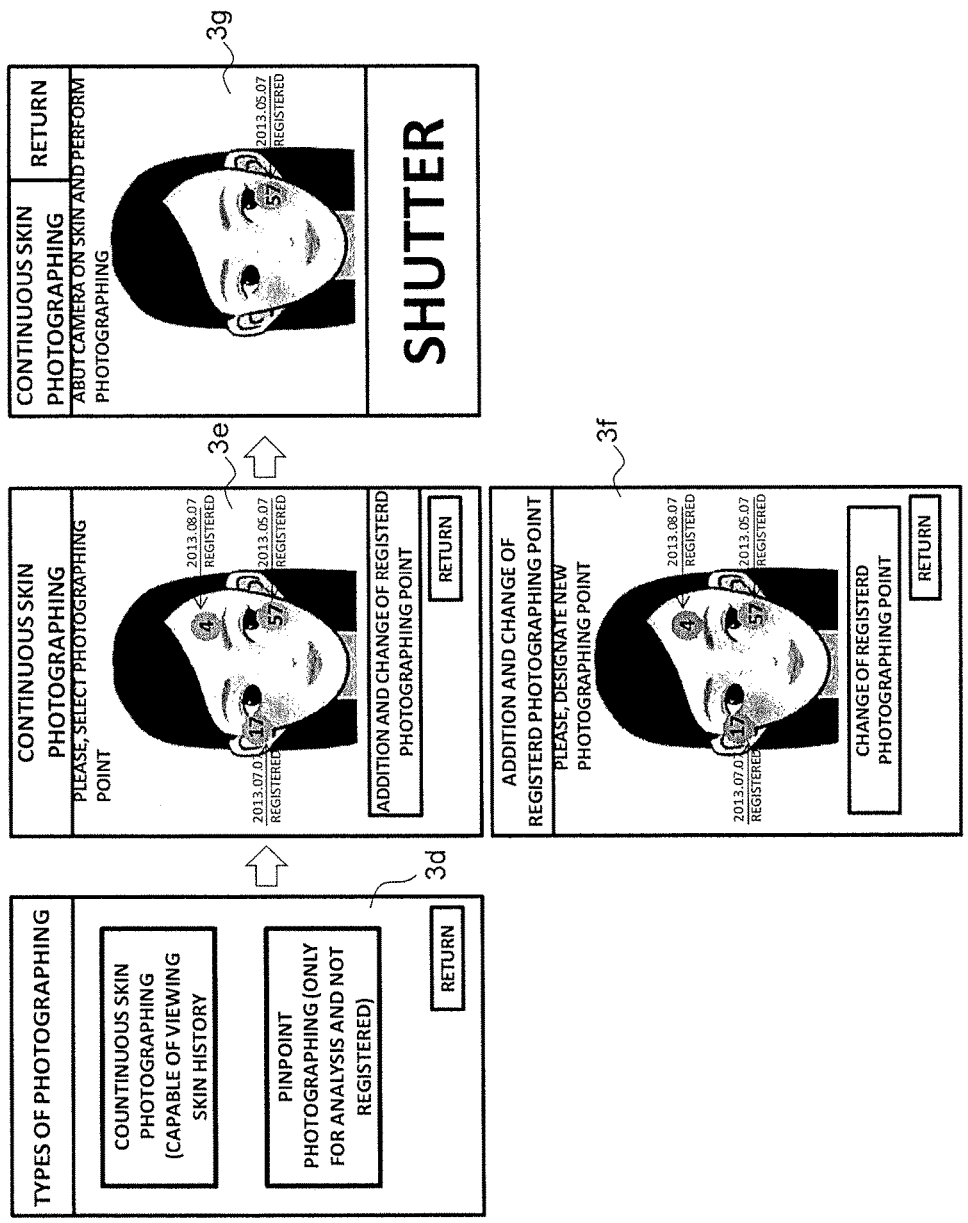

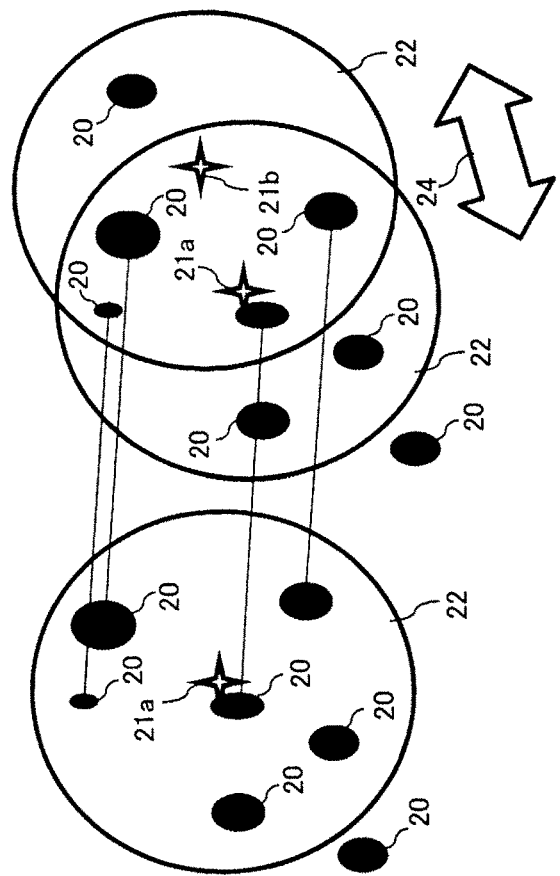
[FIG. 9]

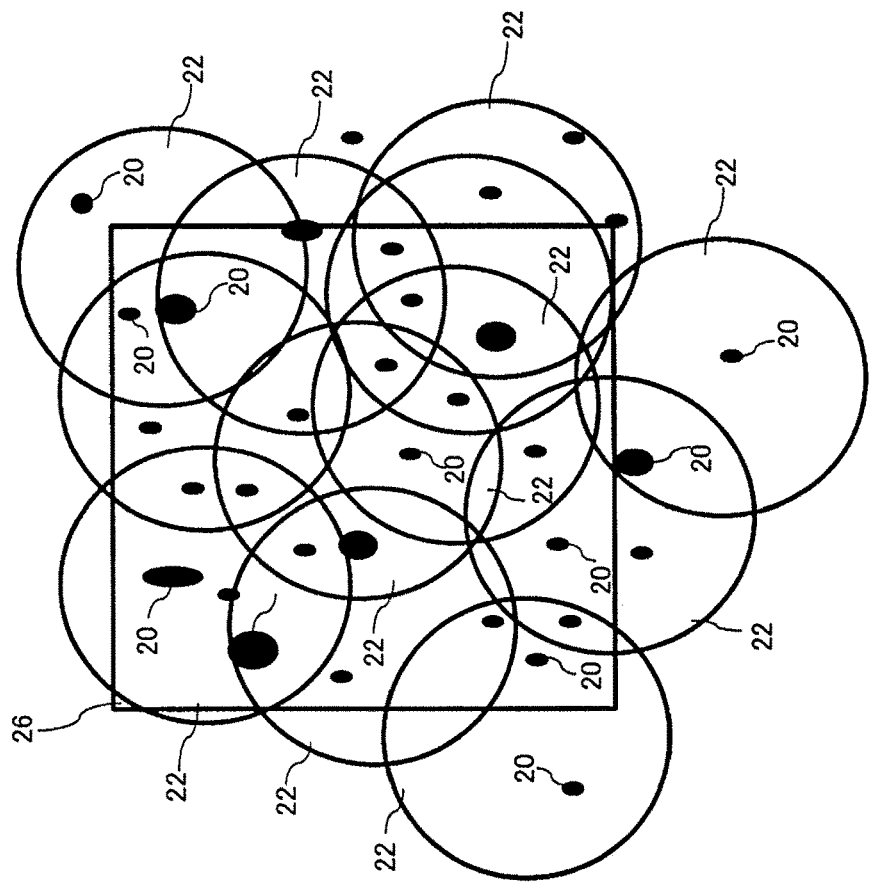
[FIG. 10]

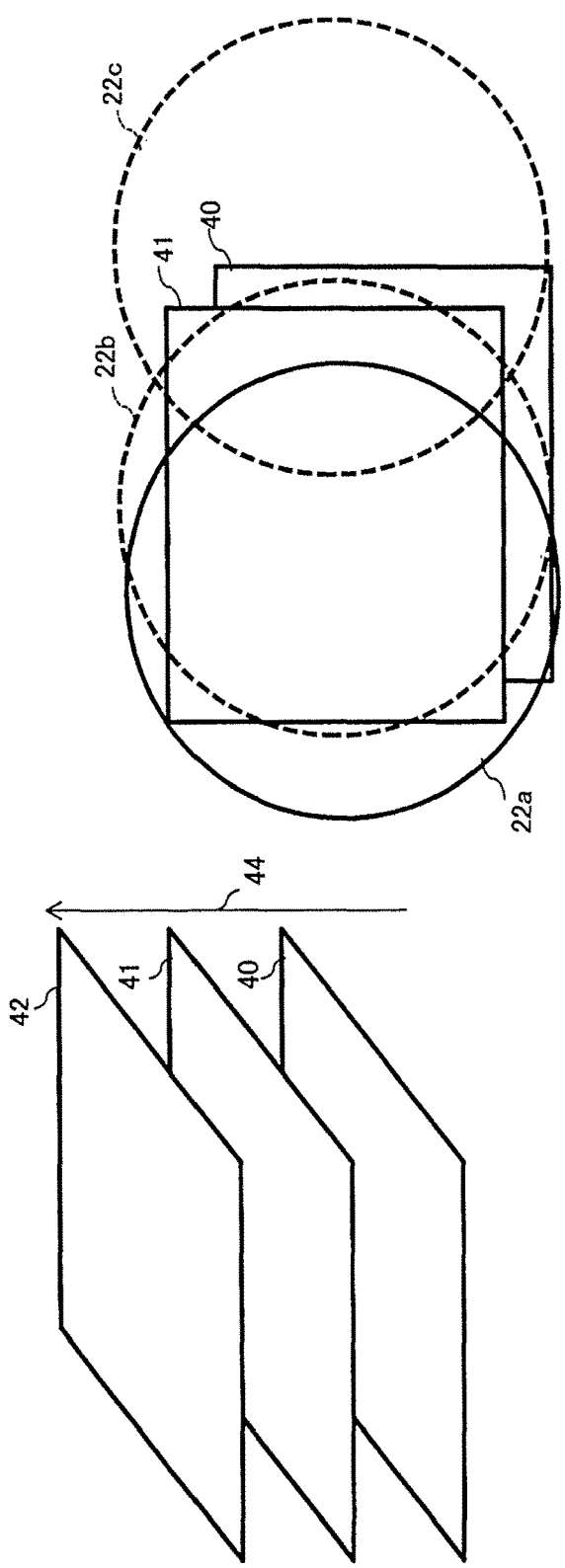

[FIG. 12]
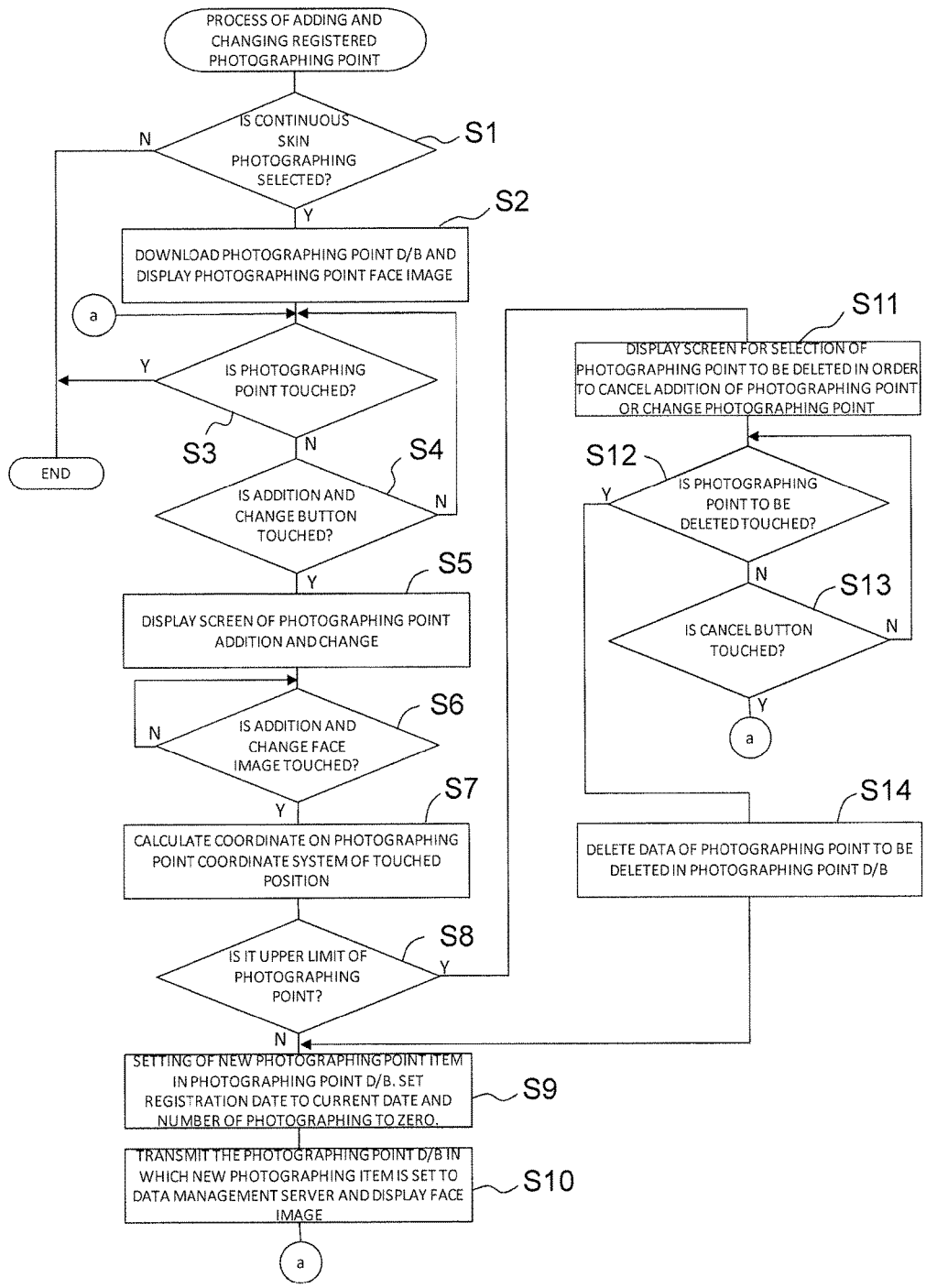

[FIG. 13]
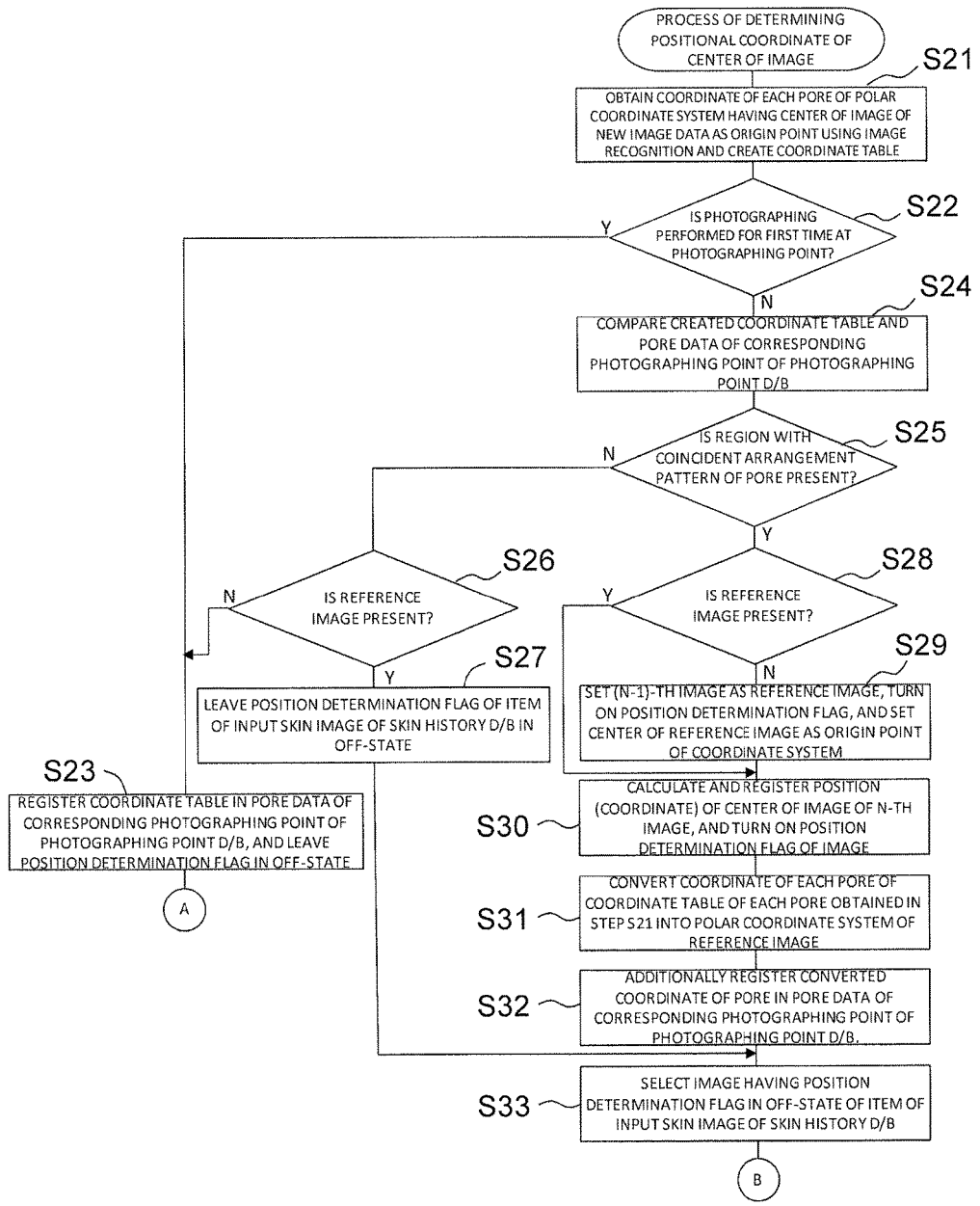

[FIG. 14]
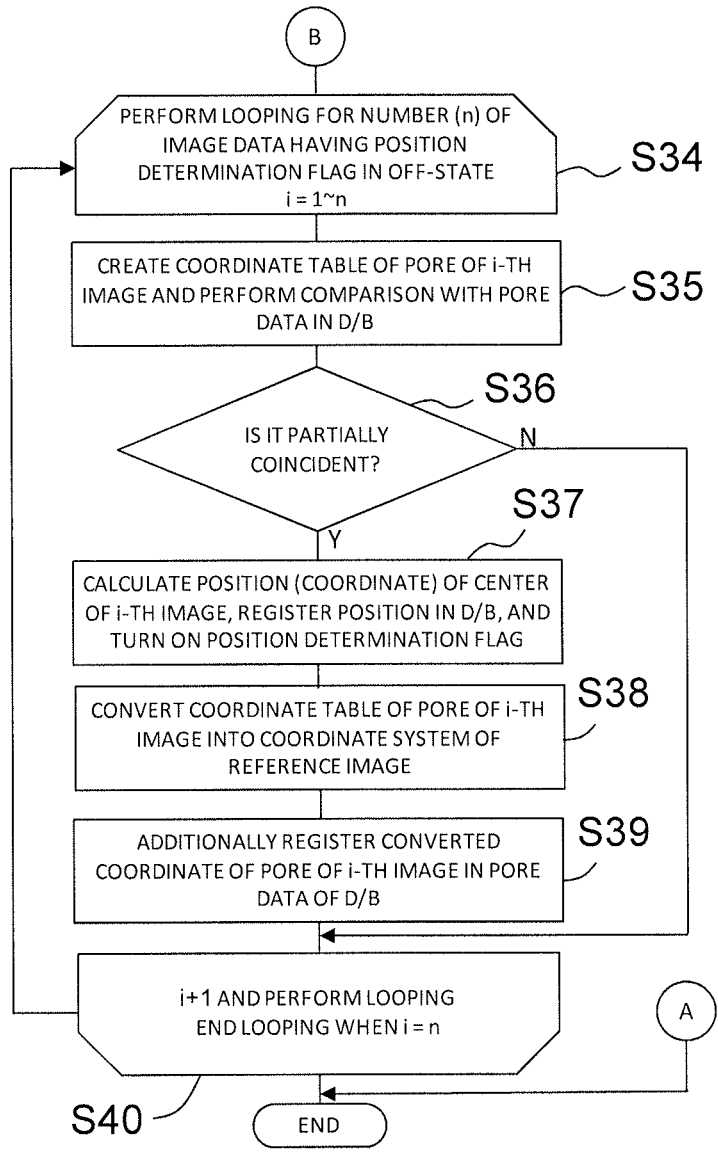

[FIG. 15]
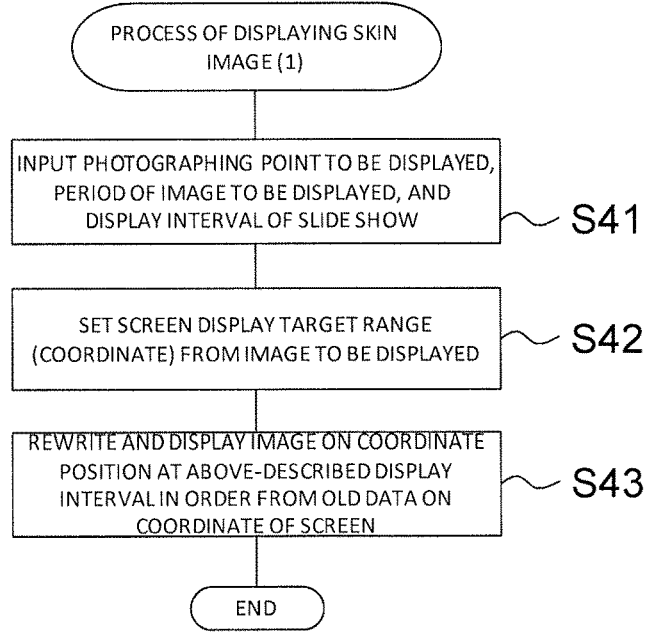
[FIG. 16]
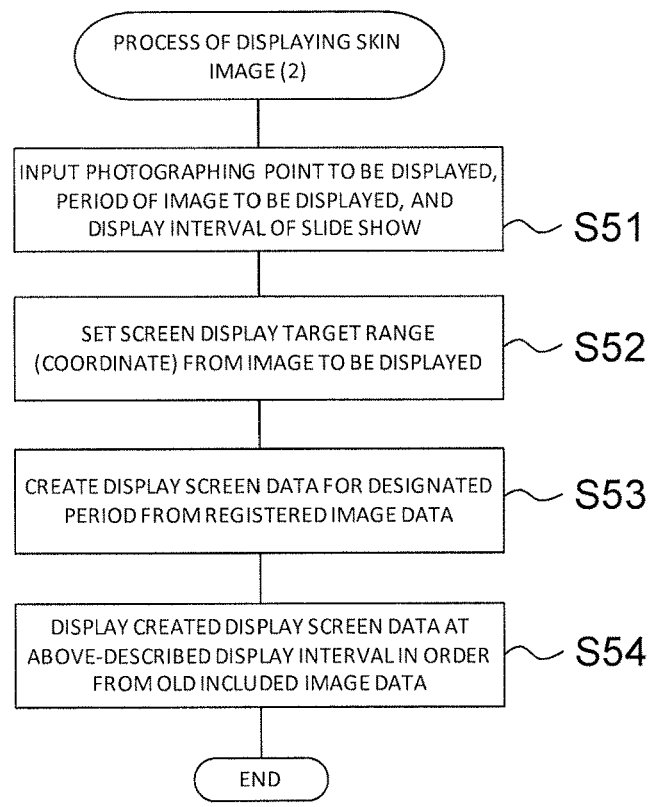

[FIG. 17]
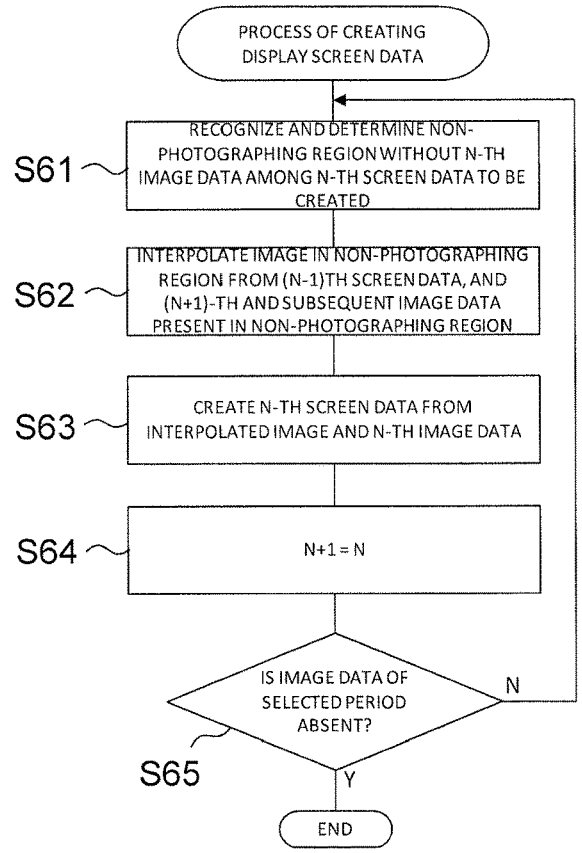
[FIG. 18]
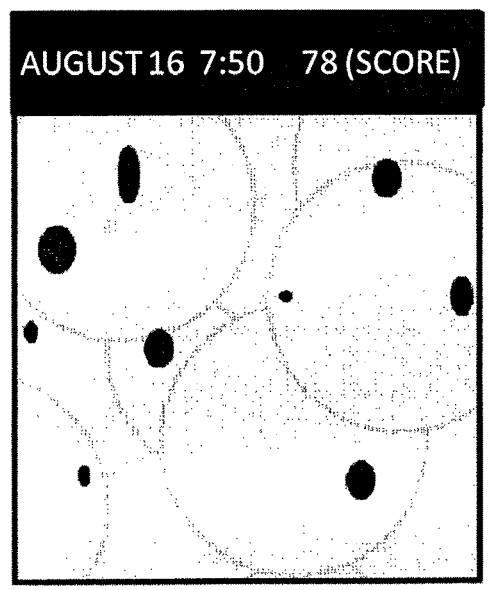

LENS INFORMATION MANAGEMENT SYSTEM FOR SURFACE CONDITION MEASUREMENT AND ANALYSIS AND INFORMATION MANAGEMENT METHOD FOR SURFACE CONDITION MEASUREMENT AND ANALYSIS

TECHNICAL FIELD

The present invention relates to an information management system for surface condition measurement and analysis and an information management method for surface condition measurement and analysis configured to sequentially photograph a surface whose condition is changed over time, for example, a surface of a skin, a surface of a leaf, a fruit, a stalk, a trunk, a root or the like of various types of plants (including vegetables or fruits), a surface of a specific part of an animal, a surface of an inorganic substance which is degraded over time or the like, as a certain condition having a possibility of being changed over time, and to manage photographed image data, a result of the analysis or the like to be viewable.

BACKGROUND ART

In general, at the time of sale of skin care cosmetics or beauty appliances (skin care device: esthetic care devices), for example, a skin is photographed in a magnified manner using a camera for a skin in order to know the skin condition, and after the skin condition is grasped, the sale of a skin care cosmetic, a facial cleansing appliance, or a tool for skin care is made in accordance with the skin condition.

In such a case, it is necessary to visit a store in which the camera for the skin is placed, and a store staff who can determine the skin condition from photographed image data and advice a method for skin care through the skin condition is present. However, it is tiresome to visit the store, and it is tiresome to visit the store and get the recommendation of the purchase of a product after receiving the above-described service, and accordingly, it is difficult to regularly photograph the skin condition.

Thus, techniques have been proposed which allow a user to be capable of photographing the skin by himself/herself by connecting a digital camera for a skin as a peripheral device to a portable wireless terminal which is accessible to the Internet via a wireless telephone line or another wireless communication line such as a mobile phone, a smartphone or a tablet, or by mounting a lens module provided with a conversion lens for photographing of the skin to a built-in digital camera of the portable wireless terminal, for example.

Further, systems have been proposed which enable analysis of a skin condition without a visit to a store for sale of cosmetics by transmitting image data photographed using a portable wireless terminal to a server of a trader that provides analysis of the skin condition from the image data of the skin (see Patent Literatures 1 to 5, for example). In this case, for example, the analysis of a measurement result is automatically performed, or measurement data is displayed to input a result of the analysis to an operator in the server that receives the measurement data.

In this case, it is necessary to make a purchase or the like of the digital camera for the skin or the lens module for the skin, but it is possible to regularly perform the measurement of the skin using such a skin measurement system without giving a great burden to the user.

In addition, it is possible to apply the above-described camera to photographing of the skin when a change in a surface condition of, for example, a leaf or a fruit of a plant as a crop, other than the skin is measured or recorded, or when a condition in long-term degradation of a surface of a structure such as a wall is measured or recorded.

In this case, it is possible to perform photographing and recording at a low cost without requiring great capital investment, for example, in a case in which a change of a surface condition of a crop is measured in a farm, or a case in which a change of a surface condition of a vegetable or a foliage plant in a home garden is photographed and recorded at an ordinary home.

CITATION LIST

Patent Literatures

Patent Literature 1: JP 2005-148797 A
Patent Literature 2: JP 2004-354207 A
Patent Literature 3: JP 2005-56165 A
Patent Literature 4: JP 2002-15068 A
Patent Literature 5: JP 2002-366651 A

SUMMARY OF INVENTION

Technical Problem

Meanwhile, it is possible to regularly photograph and analyze the same position of the face, for example, to store a change in skin conditions, and to determine whether a skin condition gets better or worse or is unchanged from the stored result in the case of performing the measurement of the skin condition.

For example, it is possible to determine a worsened condition of a skin is turned into a favorable condition through use of a skin care product or the like. In addition, it is possible to determine whether a spot or the like gets darkened or widened, or reversely, whether the spot is lightened or narrowed.

Here, for example, the skin of the face is a greatly curved surface, and thus, it is difficult to photograph a wide range in a uniformly magnified condition, and basically, a narrow range is photographed. In this case, it is difficult for the user to photograph a location which is the same as a location of being precedently photographed even in the case of photographing the skin, for example, about once or twice a day, and further, it is difficult to photograph the same location when a photographing interval increases. In addition, when a plurality of points are regularly photographed, each position of the points becomes easily vague.

When there is a relatively clear spot, it is possible to perform the photographing while confirming a position of the spot using a mirror, but the photographing position is still somewhat deviated for each photographing. Accordingly, it is considered that a case is also present in which it is possible to read a change in color or shape of the spot from skin images which has been regularly and sequentially photographed, but there is still a possibility that it is difficult to understand which spot is reflected on the image depending on a photographing range in a case in which a plurality of spots are adjacently present. In addition, when a partially worsened part is present in a condition of skin texture, it is difficult to determine whether a change is a change in the skin condition according to the passage of time or a change according to a difference in photographing positions between a case in which a worsened part is reflected and a case in which the worsened part is not reflected. Accordingly, it is difficult to grasp the change in the skin condition texture or the spot according to the passage of time even when the skin is regularly photographed.

In addition, when the image data of the skin that has been regularly photographed is stored, there is a possibility that it is possible to view how the skin condition is improved by displaying the image data as a moving image or a slide show. Accordingly, there is a possibility of attracting an interest of the user and acquiring an increase of users. In addition, it is possible to encourage the user to regularly photograph the skin.

However, the photographing positions of the photographed images are vertically and horizontally deviated every time of photographing, and the vertical and horizontal shaking is great even in a case in which the photographing positions are relatively gathered so that it is impossible to view the images as a moving image, and it is difficult to understand the connection between preceding and subsequent slides even at the time of being viewed as a slide show because there is the deviation in every photographing position, and accordingly, the change of the skin condition is not always confirmable. In addition, when the photographing position is not gathered, there is a case in which an overlapping part is not present between the preceding slide and the subsequent slide, and the display is performed in a state in which a roughened point and a favorable point of the skin are mingled, for example, and accordingly, it is difficult to confirm the change in the skin condition.

Even in a case in which the plant or the like is photographed instead of the skin, the same problem as in the above-described case of photographing of the skin is generated basically except for the case of photographing by fixing the camera using a tripod or the like.

The present invention has been made in view of the above-described circumstances, and an object thereof is to provide an information management system for surface condition measurement and analysis and an information management method for surface condition measurement and analysis that make possible the effective utilization of image data photographed when a surface as an object is photographed regularly and continuously and that can be made capable of displaying as a video or a slide show.

Solution to Problem

An information management system for surface condition measurement and analysis of the present invention includes: photographing means that photographs a surface serving as an object to be measured without fixing a photographing position and generates image data;

image storage means that stores the image data and a photographing date of the image data; and position determination means that compares a plurality of the image data stored in the image storage means, and determines relative positions of the plurality of image data in a single coordinate system when the plurality of image data, obtained from a plurality of times of photographing performed at an interval using the photographing means, of which photographing positions on the surface serving as the object to be photographed are deviated are stored in the image storage means, in which, the respective image data of which the relative positions in the coordinate system are determined can be arranged and displayed at the relative positions in the coordinate system in an order of the photographing date.

When a nearly coincident image region is present between the image data to be compared with each other, it is preferable that the position determination means determine relative positions of the plurality of image data in the single coordinate system based on the image region in the above-described configuration of the present invention.

In addition, in the above-described configuration of the present invention, it is preferable that an overlap detection means that compares the image data being sequentially stored in the image storage means, and determines whether the image regions nearly coinciding with each other are present in the image data be provided, the position determination means set the coordinate system having one of the image data as a reference when the image regions nearly coinciding with each other are present, and determine a position in the coordinate system of another image data in a state in which the image region that nearly coincides with the one image is superposed, the overlap detection means compare the image data of which the position of the coordinate system is already determined by the position determination means, and the image data of which the position of the coordinate system is not yet determined, and determine whether the image regions nearly coinciding with each other is present, and when the image data is present, which has the undetermined position of the coordinate system and the nearly coincident image region with the image data with the determined position of the coordinate system, the position determination means determine the position of the coordinate system of the image data, which has the undetermined position of the coordinate system, based on a mutual positional relation between the image data when the image data with the determined position of the coordinate system and the image data with the undetermined position of the coordinate system are arranged such that image regions nearly coinciding with each other overlap each other.

An information management method for surface condition measurement and analysis which is performed by an information management system for surface condition measurement and analysis provided with photographing means that photographs a surface serving as an object to be measured without fixing a photographing position and generates image data, and image storage means that stores the image data and a photographing date of the image data, the method includes:

a position determination step of comparing a plurality of the image data stored in the image storage means and determining relative positions of the plurality of image data in a single coordinate system when the plurality of image data, obtained from a plurality of times of photographing performed at an interval using the photographing means, of which photographing positions on the surface serving as the object to be photographed are deviated are stored in the image storage means, in which, the respective image data of which the relative positions in the coordinate system are determined can be arranged and displayed at the relative positions in the coordinate system in an order of the photographing date.

In the above-described configuration of the present invention, it is preferable that, when a nearly coincident image region is present between the image data to be compared with each other, relative positions of the plurality of image data in the single coordinate system be determined based on the image region in the position determination step.

In addition, in the above-described configuration of the present invention, it is preferable that an overlap detection step of comparing the image data being sequentially stored in the image storage means, and determining whether the image regions nearly coinciding with each other are present in the image data be included, the coordinate system having one of the image data be set as a reference when the image regions nearly coinciding with each other are present, and a position in the coordinate system of another image data in a state in which the image region the image region that nearly coincides with the one image is superposed be determined in the position determination step, the image data of which the position of the coordinate system is already determined by the position determination means, and the image data of which the position of the coordinate system is not yet determined be compared to determine whether the image regions nearly coinciding with each other is present in the overlap detection step, and when the image data is present, which has the undetermined position of the coordinate system and the nearly coincident image region with the image data with the determined position of the coordinate system, the position determination means determine the position of the coordinate system of the image data, which has the undetermined position of the coordinate system, based on a mutual positional relation between the image data when the image data with the determined position of the coordinate system and the image data with the undetermined position of the coordinate system are arranged such that image regions nearly coinciding with each other overlap each other.

According to such a configuration, the relative positions of the respective photographed images are determined from the overlapping state of the photographed images, and thus, it is possible to determine whether it is an image in which a roughened part of the skin and an unroughened part are separately taken or the skin is turned into a state in which the roughened part is no longer roughened as time passes when the surface serving as the object to be photographed is set to the surface of the skin, for example.

Accordingly, in the case of regularly photographing the skin, it is possible to determine the change in the skin condition caused by the passage of time even when the photographing positions somewhat vary. That is, it is possible to grasp the distribution of the skin condition to some extent within a range in which the image data is arranged from the data with the determined position among the respective image data even if there is a positional deviation in the image data in which the skin is photographed, without enabling photographing to be performed at the same position of the skin using an arbitrary means every time, and it is possible to determine whether the change in the skin condition is caused by the positional difference within the photographing range of the image data or caused by the passage of time.

Accordingly, it is possible to easily notice the change in the skin condition caused by the passage of time by allowing a position, as same as possible, to be intentionally photographed, for example, without providing a mechanism that forcefully sets the photographing range of the skin to be the same.

In addition, even when the surface as the object is set other than the surface of the skin, it is possible to understand whether the surface condition is changed due to the passage of time or due to the position, and easily notice the change in the skin condition caused by the passage of time by allowing a position, as same as possible, to be intentionally photographed in the same manner, without fixing the camera using the tripod or the like. Incidentally, examples of the object other than the skin include surfaces of various types of plants, and particularly, surfaces of leaves or fruits, or the like, and a surface of an inorganic substance may be used, and it is possible to set an object whose surface condition is changed over time due to growth, disease, degradation or the like.

In addition, the image storage means is not necessarily a single device, and may be configured to include temporary image storage means such as a buffer that temporarily holds a photographed image and image storage means in which the image temporarily stored in the above-described image storage means is moved and stored. In this case, it may be configured such that preceding image data, which is compared with an image in which a position has been already determined at the same time of being photographed, is stored in the temporary image storage means. Further, it may be configured such that image data which has an undetermined position even after being compared with the image data with the determined position is stored in the temporary image storage means.

In addition, in the information management system for surface condition measurement and analysis of the present invention, it is preferable that, when it is determined whether the image regions nearly coinciding with each other is present between the image data, the overlap detection means extract a position of a characteristic point of the image data in response to a type of an object photographed by the photographing means, compare an arrangement pattern of the characteristic point for each of the image data, and determine that image regions nearly coinciding with each other is present when a part in which the arrangement patterns of the characteristic points nearly coincide with each other is present.

In addition, in the information management method for surface condition measurement and analysis of the present invention, it is preferable that, when it is determined whether the image regions nearly coinciding with each other is present between the image data, a position of a characteristic point of the image data be extracted in response to a type of an object photographed by the photographing means, an arrangement pattern of the characteristic point be compared for each of the image data, and image regions nearly coinciding with each other be determined to be present when a part in which the arrangement patterns of the characteristic points nearly coincide with each other is present in the overlap detection step.

According to such a configuration, the position of the characteristic point in the respective image data is extracted to recognize the arrangement pattern of the characteristic point, and thus, it is possible to easily recognize whether the overlapping part is present between the image data. Incidentally, it is preferable that the characteristic point be present almost all the surfaces as the objects and be recognizable from the image data. For example, the center of a pore is considered as the characteristic point in a case in which the surface as the object is set to the skin. In addition, it is possible to set a branch point of a leaf vein as the characteristic point in a case in which the object is the leaf of the plant.

Incidentally, when a leaf to be photographed can be identified from a plurality of leafs, there is a possibility that it is possible to specify a position of a surface of the leaf mainly from the branch points of midvein among the thick midvein and thin lateral veins configuring the left veins, and it is possible to cope with a leaf which is thick so that lateral veins thereof can hardly confirmed from the surface. In addition, when there are patterns or irregularities on the surface of the fruit, it is possible to determine the characteristic point from such patterns and irregularities. Even in the case of the inorganic substance, it is possible to determine the characteristic point, for example, using marble or the like with a change in color.

In addition, in the information management system for surface condition measurement and analysis of the present invention, it is preferable that the surface serving as the object to be photographed by the photographing means be a surface of a skin, and the characteristic point to be extracted from the image data by the overlap detection means be a predetermined part of each pore on the skin surface.

In addition, in the information management method for surface condition measurement and analysis of the present invention, it is preferable that the surface serving as the object to be photographed by the photographing means be a surface of a skin, and the characteristic point to be extracted from the image data in the overlap detection step be a predetermined part of each pore on the skin surface.

According to such a configuration, the pore is extracted as the characteristic part even when the skin image in which the characteristic part serving as the object to be compared is scarce is set as the image, and thus, it is possible to search a part having an image nearly the same with each other by comparing two skin images through the arrangements of the respective pores, and it is possible to determine the overlap among the respective image data. Incidentally, the predetermined part is a position at which, for example, any one of the center position, the barycentric position, and the right end position, the left end position, the upper end position and the lower end position on the image of the pore is set. Here, for example, the position of the characteristic point is set as the coordinate of the coordinate system, and thus, a predetermined position is set as the characteristic point when there is an area in the photographed part (pore) including the characteristic point.

In addition, basically, when the nose, eyes, ears, mouth or the like is exempted and the other part is photographed in the case of observing the skin of the face, for example, the image without particular characteristic is obtained, and it is difficult to determine any part of the respective images overlapping each other in the case of photographing the plurality of images while shifting the positions, but it is possible to relatively easily determine any part of the respective images overlapping each other using the arrangement of the pores. However, the pores are nearly uniformly arranged on the skin although there are somewhat changes depending on a location, for example, and a healthy pore is closed when there is no hair, and thus, the recognition thereof is difficult. Thus, the hair generated from the pore of the skin is recognized, and an end portion with the thick hair is considered as the pore using a fact that the hair has a shape in which a distal end side is thin and a pore side is thick, and then, a predetermined position of this pore is set as the characteristic point. In this case, the arrangement pattern of the pores is different depending on the location on the skin through the recognized pores with hair and the unrecognized pores without hair.

In addition, in the information management system for surface condition measurement and analysis of the present invention, it is preferable that the surface serving as the object to be photographed by the photographing means be a surface of a skin, and the characteristic point to be extracted from the image data by the overlap detection means be a predetermined part of each spot of equal to or smaller than a predetermined size on the skin surface.

In addition, in the information management method for surface condition measurement and analysis of the present invention, it is preferable that the surface serving as the object to be photographed by the photographing means be a surface of a skin, and the characteristic point to be extracted from the image data in the overlap detection step be a predetermined part of each spot of equal to or smaller than a predetermined size on the skin surface.

According to such a configuration, it is possible to determine the overlap among the respective image data from the arrangement pattern of the spots as the characteristic point even when the skin image in which the characteristic part serving as the object to be compared is scarce is set as the image.

Here, the spot of equal to or smaller than a predetermined size is a small spot to be formed mainly in a part of the pore, and in which melanin is retained in the part of the pore. Accordingly, when the pore is set as the characteristic point as described above, it is possible to replace the above-described method of recognizing the pore through the end portion of the hair on the skin side with the method of recognizing the spot of equal to or smaller than the predetermined size as the pore, or use both the methods in a combined manner. In the case of using the combination, it is possible to compare the arrangement patterns by, for example, dividing the characteristic points into a point only with the hair, a point only with the spot, and a point with both the hair and spot and the like.

In addition, in the information management system for surface condition measurement and analysis of the present invention, it is preferable that image display means that displays the image data stored in the image storage means in the order of the photographing date of the image data be provided, and the image display means arrange the respective image data of which the coordinate system is set on a display screen and the positions in the coordinate system are determined at the positions of the coordinate system, and display the image data in the order of the photographing date.

In addition, in the above-described configuration of the present invention, it is preferable that the image display means display the image data on a frontmost surface in the order of the photographing date to be held in a state of displaying a part of the image data to be displayed on the frontmost surface, which is displayed prior to relevant image data, that does not overlap with the relevant image data to be displayed on the frontmost surface.

In addition, in the above-described configuration of the present invention, it is preferable that the image display means generate image data interpolated from the image data having the preceding or subsequent photographing date at time of displaying the image data in the order of the photographing date when a display range to display relevant image data includes a part in which displayed relevant image data is present and a apart in which the relevant image data is absent, and the image data having the preceding or subsequent photographing date than the displayed relevant image data is present in the part in which the relevant image data is absent, and display the interpolated image data in the part of the display range in which the displayed image data is absent.

In addition, in the information management method for surface condition measurement and analysis of the present invention, it is preferable that image display step that displays the image data stored in the image storage means in the order of the photographing date of the image data be provided, and in the image display step, the respective image data of which the coordinate system is set on a display screen and the positions in the coordinate system are determined be arranged at the positions of the coordinate system to display the image data in the order of the photographing date.

In addition, in the above-described configuration of the present invention, it is preferable that the image data be displayed on a frontmost surface in the order of the photographing date to be held in a state of displaying a part of the image data to be displayed on the frontmost surface, which is displayed prior to relevant image data, that does not overlap with the relevant image data to be displayed on the frontmost surface in the image display step.

In addition, in the above-described configuration of the present invention, it is preferable that image data interpolated from the image data having the preceding or subsequent photographing date be generated at time of displaying the image data in the order of the photographing date when a display range to display relevant image data includes a part in which displayed relevant image data is present and a apart in which the relevant image data is absent, and the image data having the preceding or subsequent photographing date than the displayed relevant image data is present in the part in which the relevant image data is absent, and the interpolated image data be displayed in the part of the display range in which the displayed image data is absent in the image display step.

According to such a configuration, the positions of the respective image data are deviated when the image data is displayed as the moving image or the slide show directly in the photographed order so that the display is performed close to severe hand shaking, but, it is possible to perform the display in which the change of the skin is sufficiently recognizable by arranging the respective image data at the coordinate positions and sequentially displaying the image data while preventing the display in the severe hand shaking state. Incidentally, the skin image with the preceding photographed order is deleted, and the skin image with subsequent photographed order is displayed as the display method when the skin image with the subsequent photographed order is displayed in a state in which at least a part thereof overlaps with the skin image with the preceding photographed order, but it is preferable that a part of the skin image with the preceding photographed order that does not overlap remain in a state in which the skin image thereof is displayed.

In this case, a state is formed in which the skin images with different photographed timings are displayed on the single display screen, but, a lot of new skin images are superimposed on a skin image with old photographed timing when the number of skin images to be displayed increases so that the old skin image has few displayed part, and eventually, the displayed skin image is switched. In addition, when more and more skin images with subsequent photographed timing are sequentially displayed, the display of the skin image with the photographed timing preceding to the displayed skin image remains around the subsequent skin image, and thus, the recognition of the change in the skin condition over time becomes easy by comparing the newly displayed skin image and the precedently displayed skin image therearound.

Incidentally, display range regulation means may be provided, which narrows down the actually displayed range of the skin in the state of allowing a range of the skin that is wider than the photographing range of the skin of the skin image to be displayed. In this case, it is preferable to set a display range in which the largest number of photographed skin images can be displayed. In addition, the display range at this time may be a narrow range than the photographing range of the skin image.

In addition, in the case of displaying the display range in which the image data is sequentially set, the entire image data of the respective display ranges (hereinafter, referred to as the display image data) is configured of a part with the image data and a part without the image data, for example. At this time, the part with the image data displays the range in which the corresponding image data and the display image data overlap each other, and the part without the image data may be configured such that the interpolated image data, which is interpolated from the image data with the preceding photographed order than the displayed image data and the subsequent image data, is created, and the interpolated image data is arranged in the part without the image data of the display image data.

In this case, the respective display image data include the part with the interpolated image data and the part with the photographed image data. In addition, it is possible to use the immediately preceding display image data as the image data for interpolation as the image data preceding to the displayed image data, for example, after the display image data is once created. In this case, it is possible to create the interpolated image data using the immediately preceding display image data including the interpolation-processed part and the image data subsequent to the image data to be displayed, and thus, the interpolation processing can be easily executed.

Advantageous Effects of Invention

According to the information management system for surface condition measurement and analysis of the present invention and the information management method for surface condition measurement and analysis, when a range, as same as possible, of a skin is photographed regularly at most in order to grasp a change in a skin condition over time, and the change of the skin condition is grasped, it is possible to more clearly grasp a change of the skin at the same position over time by grasping relative positions of the respective skin images even if there is a positional deviation in the range of the skin photographed in the respective photographed skin images.

BRIEF DESCRIPTION OF DRAWINGS

FIG. 1 is a schematic block diagram illustrating an information management system for surface condition measurement and analysis according to an embodiment of the present invention.

FIG. 2 is a schematic diagram illustrating an example of conversion lens.

FIG. 3 is a block diagram illustrating the information management system for surface condition measurement and analysis.

FIG. 4 is a block diagram illustrating a data management server of the information management system for surface condition measurement and analysis.

FIG. 5 is a diagram for describing a user data database of the data management server.

FIG. 6 is a diagram for describing a measurement data database of the data management server.

FIG. 7 is a diagram for describing a continuous skin photographing method in the information management system for surface condition measurement and analysis.

FIG. 8 is a diagram for describing the continuous skin photographing method in the information management system for surface condition measurement and analysis.

FIG. 9 is a diagram for describing overlapping two image data through arrangement patterns of reflected pores.

FIG. 10 is a diagram for describing a display method as a slide show of image data.

FIGS. 11(*a*) and 11(*b*) are diagrams for describing another display method as the slide show of the image data.

FIG. 12 is a flowchart for describing a process of adding and changing a registration photographing point in the information management system for surface condition measurement and analysis.

FIG. 13 is a flowchart for describing a process of determining a positional coordinate of the center of an image in the information management system for surface condition measurement and analysis.

FIG. 14 is a flowchart for describing a process of determining a position of an undefined image in the process of determining the positional coordinate of the center of the image in the information management system for surface condition measurement and analysis.

FIG. 15 is a diagram for describing a method of processing display of the image data in the information management system for surface condition measurement and analysis.

FIG. 16 is a diagram for describing another method of processing the display of the image data in the information management system for surface condition measurement and analysis.

FIG. 17 is a diagram for describing a process of creating display screen data which is created by interpolating display screen data to be displayed in display processing.

FIG. 18 is a diagram for describing a screen configuration of a smartphone which performs slide show display of the image data.

DESCRIPTION OF EMBODIMENTS

Here, an embodiment of the present invention will be described with reference to the drawings.

An information management system for surface condition (skin condition) measurement and analysis of and an information management method for surface condition (skin condition) measurement and analysis according to the embodiment allows a user to recognize a condition of his/her own skin by providing service in which a result of analysis of the own skin condition can be obtained from measurement data of a skin condition measurement device to the user of the skin condition measurement device who is a member of the information management system for surface condition measurement and analysis at a low cost (for example, for free or with a relatively low membership fee).

At this time, since the skin condition can be understood at a low cost, the number of sales of the skin condition measurement device is increased, the user is encouraged to frequently perform the measurement of the skin condition, the analysis result is acquired from the measurement data, and the measurement data is frequently collected from many users. In this case, skin care products including cosmetics or the skin care device are recommended to use, and then, the user is allowed to grasp that the skin condition is improved, thereby facilitating the sale of the skin care products or the skin care device.

In addition, when a lot of measurement data of skin conditions is collected, it is possible to allow collected data to be used in development of various types of skin care products by manufacturers of cosmetics or sales companies (cosmetic companies) by paying a fee. At this time, it is possible to enable more effective use of the measurement data by providing an added value by adding not only the measurement data but also collateral data such as a skin care product or a skin care device that is being used by a user, and further, an approximate age, a residential area, annual income, an occupation or the like of the user. Accordingly, it is possible to make profits not only from a user who purchases the skin condition measurement device or the like but also from a secondary user of data such as the cosmetic company that uses the measurement data as above.

As illustrated in FIG. 1, the information management system for surface condition measurement and analysis of the present embodiment is provided with a smartphone 3 serving as a user client to which a skin condition measurement device 1 can be connected, a data management server 5 which can be connected to the smartphone 3 via the internet 4 (network), and a computer system of a partner company such as a cosmetic company serving as a contractor client 6.

The smartphone 3 is provided with a built-in digital camera, a flash memory serving as storage means (a storage device) which stores photographed image data 22 (illustrated in FIGS. 9 and 10), other data, an application or the like in the digital camera, a display which displays an image or the like, and a control unit which executes an OS or the application. The display displays the photographed and stored image data 22 as a moving image or a slide show as will be described later.

The skin condition measurement device 1 may be a camera for a skin (skin photographing means), for example, which is connected using an USB or is wirelessly connected to the user client such as the smartphone 3 or a PC. The camera for the skin has an optical system configured of an imaging lens and an LED for illumination (not illustrated), and is provided with a sensor unit 11, which detects an image to be obtained from the optical system, a control unit 12, and a universal serial bus (USB) interface 13. The illumination LED is capable of emitting light of two colors, for example, and is capable of irradiation of skin color light (light with yellow stronger than white) and white color light in a switching manner. At the time of irradiation of the skin color light, a skin condition can be distinctly photographed, and analysis of a condition of skin texture (texture) becomes easy.

In addition, at the time of illumination of the white color light, relatively blue light becomes stronger than the above-described skin color light, and it is possible to obtain the image data 22 from which a spot is easily recognized.

The skin condition measurement device 1 serving as the camera for the skin enables photographing in a switching manner between a texture mode and a spot mode, and is provided with a changeover switch to switch the mode. It is configured such that data indicating the texture mode or the spot mode is output to the smartphone 3 in relation to imaging data serving as measurement data obtained by the camera for the skin.

Incidentally, it is configured such that two polarizing plates of which polarization directions are orthogonal to each other are used in the LED of the white color light for photographing of the spot, and the polarizing plate (a first polarizing plate) is not used in the LED of the skin color for photographing of the texture. When the two polarizing plates of which polarization directions are orthogonal to each other are used, the illumination light is polarized and the illumination light reflected by the skin is photographed again through the polarizing plate, and accordingly, the light reflected from the skin surface is reduced, and it is possible to form a state in which the reflected light that is reflected inside a skin surface layer portion where the spot is present is mainly photographed. In addition, the analysis of the skin color may use the LED of the skin color light, for example by performing color correction.

Incidentally, the data communication between the camera for the skin, which is the skin condition measurement device 1, and the smartphone 3 is not limited to the use of the USB, but may use another wired serial or parallel communication, or wireless Bluetooth®, Wi-Fi, Near Field Communication (NFC) and the like.

In addition, a well-known evaporimeter, which measures transepidermal water evaporation amount or a melanin meter that measures a melanin amount of the skin, for example, may be used as the skin condition measurement device 1 other than the above-described camera for the skin.

In addition, a device that measures ultraviolet rays (UV) (a UV checker) may be connectable to the smartphone 3 as an environment measurement sensor although not being a device that directly measures the skin condition. Incidentally, when influence of the ultraviolet with respect to the skin is observed, it is preferable that the UV checker be capable of consecutively outputting separate independent numerical data for UV-A, which relates to melanin generation and UV-B which causes inflammation, respectively.

In addition, when the skin condition measurement device 1 is the camera for the skin configured to photograph the skin, the digital camera built in the smartphone 3 may be used. In this case, the lens module, which is provided with a conversion lens configured to photograph the skin using the digital camera of the smartphone 3, the above-described illumination LED, the polarizing plate, and the control unit that controls lighting of the LED. In this case, the photographed image data 22 is stored in the smartphone 3, and thus, the data communication between the smartphone 3 and the lens module is unnecessary, but the lighting of the LED may be controlled from the smartphone 3 side through the communication with the above-described control unit, for example.

FIG. 2 illustrates an example of the smartphone 3 provided with such a conversion lens.

In this example, provided are the smartphone 3 and a lens module 80, which includes a conversion lens 81, formed of two lenses 81a and 81b and mounted to a camera 72 of the smartphone 3 to magnify and close up the skin, and an illumination LED 82 for photographing.

The smartphone 3 is provided with the camera 72 to photograph a subject, a flash memory 74, in which image data photographed by the camera 72 or other data is stored, and a control unit 73 to control the camera 72, the flash memory 74 and various types of electronic components of the smartphone 3.

The lens module 80 is provided with the above-described conversion lens 81 and LED 82, a LED drive circuit 84 to drive the LED 82, and a housing 80a to house these members. In the housing 80a, the two lenses 81a and 81b of the conversion lens 81 are supported by barrels 90a, and are arranged in front of a master lens (not illustrated) of the camera 72 such that an optical axis of the master lens of the camera 72 and optical axes of the two lenses 81a and 81b nearly match each other.

In addition, the housing 80a is provided with a lens housing 90 on a front side (subject side) of the barrel 90a. The lens housing 90 is configured such that a distal end surface functions as an abutting portion 90b which abuts on the skin at the time of photographing of the skin as the subject, and external light is shielded in a state in which the abutting portion 90b abuts on the skin. In addition, an opening portion 80c is formed in the abutting portion 90b such that a part of the skin facing the opening portion 80c is photographed.

The barrel 90a is fixed to a base end side of the lens housing 90 (the side to be mounted to the camera 72) inside the housing 80a in the state of supporting the conversion lens 81 which is formed of the lens 81a and the lens 81b. In addition, a circuit board 83, which is provided with the LED 82 to irradiate the opening portion 80c of the abutting portion 90b of the lens housing 90 with the illumination light for photographing, and the LED drive circuit 84 to drive the LED 82, is supported inside the housing 80a.

In addition, the single LED 82 is provided in the circuit board 83, for example, but a plurality, for example, of the LEDs 82 may be provided to illuminate the skin from different positions. In addition, the lens module 80 is provided with a power circuit 88 including a battery to supply power to the LED 82, the LED drive circuit 84 and the like, and a power switch (not illustrated).

The above-described aspect illustrates an example in which the smartphone and the conversion lens are combined, but an aspect is also possible in which the function of the conversion lens is incorporated in the smartphone through high functionality of an optical system.

In addition, when the external light such as solar light and interior light is used for the illumination instead of using the dedicated LED, for example, a lens module, which is configured of a transparent lens barrel and a conversion lens set to the lens barrel, may be used. In this case, the LED or the like, which requires power, is not configured, and thus, it may be enough if a lens barrel abutting on the skin and a lens provided to the lens barrel are configured at least.

The user client is basically the smartphone 3, but may be a device provided with a general-purpose arithmetic processing unit (for example, a CPU) that executes processing based on a program of a notebook computer, a tablet type (pad type) computer, or the like. A portable device, which can be connected to the internet 4 as a network via the wireless telephone line or other wireless communication lines, is preferably used as the user client.

The smartphone 3 serving as the user client is capable of using, for example, a portable wireless telephone line as the wireless communication, and also capable of using the wireless LAN (Wi-Fi), and can be connected to the internet 4 as the network using the wireless communication so as to function as a wireless mobile terminal (wireless mobile client).

In addition, the smartphone 3 is configured such that, for example, an application downloaded and installed (hereinafter, simply referred to as a dedicated application 5j (illustrated in FIG. 3) can be executed, and an application for measuring the skin condition is downloaded from the data management server 5 to the smartphone 3 as the dedicated application 5j in the present embodiment.

The dedicated application 5j to be executed in the smartphone 3 includes four functions as illustrated in FIG. 7. That is, there are four functions including esthetic diagnosis, esthetic care, esthetic life, and esthetic makeup. The esthetic diagnosis is configured such that various kinds of measurement are possible using various kinds of measurement devices (sensors) to be connected to the smartphone 3 via the USB interface 13. Each of the measurement devices can be used when being connected to a USB terminal of the smartphone 3 in which the dedicated application 5j is installed. In addition, measurement using each different sensor can be executed by switching the various types of measurement devices, and it is possible to measure mainly the skin condition. The various types of the measurement devices function as the above-described skin condition measurement device 1.

In addition, measurement results of the various types of the measurement device can be transmitted to and stored in the data management server 5, and also the skin condition can be analyzed from the measurement data.

The esthetic care is configured such that various kinds of skin care devices can be used when being connected to the smartphone 3. It is possible to leave use history through the connection with the smartphone 3, and the various types of the skin care device can be controlled by setting the smartphone 3 to be in the state of being capable of data communication with the data management server 5.

The esthetic life is directed to daily life while the esthetic diagnosis is mainly directed to the skin, and is configured to allow a device for checking the amount of ultraviolet light or oral malodor to be connected to the USB terminal of the smartphone 3. The esthetic make-up is configured to mainly provide information relating to make-up.

Incidentally, FIG. 7 illustrates display screens 3a, 3b and 3c serving as display means of the smartphone 3, and the display screen 3a indicates a main menu, the display screen 3b indicates an esthetic diagnosis menu which is selected from the main menu, and the display screen 3c indicates a skin diagnosis menu which is selected from the esthetic diagnosis menu as will be described later. Incidentally, BMI in the skin diagnosis menu is an acronym of Body, Mass and Index, is calculated by body weight (kg)÷height (m)÷height (m), and indicates a degree of obesity. In addition, the whitening is determined from a skin image, and each of skin elasticity, skin moisture and skin oil is measured by the skin condition measurement device 1 provided with the measurement sensor.

The dedicated application 5j for the skin condition measurement, which is executed by a control unit 32 (arithmetic processor) of the smartphone 3, stores the image data 22 (skin image data) imaged using the digital camera 31 and the lens module of the smartphone 3 as the skin condition measurement device 1 in the flash memory, as described above, and outputs the image data to the data management server 5 of the internet 4. In addition, the dedicated application 5j also has a function as analysis result display means that receives a result of analysis data, which is the result from analysis of the measurement data, for example, to be transmitted from the data management server 5, and displays the result on the display of the smartphone 3.

In addition, the above-described dedicated application 5j is configured so as to perform member registration in which user data (personal information) is input to become a member (user) who uses the information management system for surface condition measurement and analysis managed by an administrator of the data management server 5, or to answer a questionnaire in which the collateral data, which does not include predetermined personal information from which an individual can be specified, is input among the user data.

In addition, the dedicated application 5j is configured to enable a request to allow browsing of the above-described respective user data, measurement data, and the analysis result data on the measurement data which are stored in the data management server 5 as will be described later.

In addition, when the requested data is received from the data management server 5, the dedicated application 5j has a function of displaying the data on the display.

As illustrated in FIG. 1, the data management server 5 is basically provided with a user data database 51 configured to store the-above described user data, a measurement data database 52 configured to store the measurement data obtained by the skin condition measurement device 1, a data analysis database 53 configured to acquire the analysis result from the measurement data, and a contractor database 54.

More particularly, the data management server 5 is provided with a control unit 5k including a CPU or the like to function as a server as illustrated in FIGS. 3 and 4. This control unit 5k is configured to allow various types of processing to be performed, and has a function as overlap detection means that compares the photographed image data 22 to recognize whether parts with overlapping positions on the skin is present and position determination means that determines each relative position of the image data 22 in which the parts with overlapping positions on the skin are present.

In addition, the user data database 51 is divided in a plurality of parts in the data management server 5, and a client (user) personal information management database 5a, a use cosmetic history database 5d, and a care chart database 5o are provided as the user data database 51.

In addition, the data management server 5 is provided with a skin history database (skin image storage means) 5b, a photographing point database 5c, and a detailed diagnosis result database 5e as the measurement data database 52.

In addition, the data management server 5 is provided with a skin reference value database 5g as the data analysis database 53. In addition, in addition, the data management server 5 is provided with a secondary data user access right management database 5h as the contractor database 54. A client ID of a user (a contractor, for example, a company that conducts development on a date for skin care such as a cosmetic company), a user ID, and a user password are set in this secondary data user access right management database 5h, and accordingly, authentication of a secondary data user is possible.

In addition, data of a user retrieval level and a user access level and billing Information are registered in the secondary data user access right management database 5h in association with the user ID. Incidentally, the billing Information is data of the billing in a case in which the secondary data user has performed the retrieval of data or acquisition of accessible data, and a usage fee of data is requested to the user based on the billing Information. In addition, the usage fee is set to be different depending on the retrieval level and an access level, the usage fee increases as the number of retrievable keywords (retrieval items) increases, and the usage fee increases as the access level. Incidentally, the retrievable item is restricted depending on the retrieval level, the accessible data is restricted depending on the access level, and the higher the level is, the less the restriction is.

In addition, the data management server 5 is provided with a device information database 5i that manages devices having the same product serial No. such that the single skin condition measurement device 1 can be shared among a plurality of the smartphones 3, in addition to the above-described databases 51 to 54. Incidentally, the product serial No. is a character string which is generated to be identifiable according to a predetermined algorithm. It is possible to determine whether the skin condition measurement device 1 is a device that can be used in this information management system for surface condition measurement and analysis using a serial No. as the character string, and a unique character string is different for each of the skin condition measurement devices 1.

The above-described each product serial No. of the skin condition measurement devices 1 and the clients ID are associated in the device information database 5i. The authentication of the serial No. is performed in the above-described manner, and when each of the skin condition measurement devices 1 has been authenticated, the serial No., which has been authenticated, is registered in association with the client ID corresponding to the smartphone 3 to which the respective devices are connected. In this case, it is configured such that, for example, the single skin condition measurement device 1 can be shared by three people, that is, the three smartphones 3 at most.

In addition, the data management server 5 is provided with a calibration database 5m configured to calibrate the camera for the skin (the image data 22) and a registered cosmetic database 5p in which various types of the cosmetics being commercially available are registered, in addition to the above-described databases 51 to 54.

A brightness rank and a calibration rank of color tone of three colors are registered in the calibration database 5m in association with each other using the image data 22 of a test chart as imaging by the camera for the skin under a predetermined condition as illustrated in Table 12, for example.

In the registered cosmetic database 5p, data of the cosmetics being commercially available is registered, and a cosmetic category, a manufacturer name, a brand name (product name), a volume, a product code (JAN code) and the like, which will be described later, are stored, and also, product data including price, a component, a recommended use amount (ml/once) and the like, which are published by the manufacturer, is registered.

As illustrated in the client personal information management database 5a of the user data database 51 of FIG. 5, the client ID, a personal user ID, a personal password, a name, a date of birth, an age, sex, address 1 (nation), address 2 (prefecture), address 3 (municipality (district)), address 4 (house number (apartment name, room number)), email address, and the billing Information (credit card information or the like) are stored in the client personal information management database 5a as data input by the user using the smartphone 3.

Incidentally, the client ID is an ID given by the data management server 5 side in association with the personal user ID, and the personal user ID is an ID which is set by the user under a condition that prevents the overlap with a personal user ID of another user. In addition, the personal password is used for the authentication of the user together with the personal user ID. Incidentally, the two client ID and personal user ID are used as the ID having one-to-one correspondence with each user, but the two IDs may be collectively used with a single ID, only the client ID may be used as the user ID, and only the personal user ID may be used as the user ID.

However, the present embodiment is configured such that the data relating to the user is managed entirely by the client ID in the case of being stored in the respective databases, and it is possible to retrieve and acquire the entire data relating to the respective users by retrieving the respective databases in which the data relating to the respective users are stored using the client ID. Accordingly, each user data is registered in association with each client ID also in the client personal information management database 5a. Incidentally, the client ID may be replaced by the personal user ID as described above.

In addition, it is configured such that the product serial No., which is input from the skin condition measurement device 1 connected to the smartphone 3, is also stored in the client personal information management database 5a as illustrated in FIG. 5. Incidentally, the product serial No. is set to be stored after being authenticated in the data management server 5, and the authentication of the product serial No. is not performed in a case in which the product serial No. is registered in the client personal information management database 5a.

As illustrated in FIG. 5, history data of a skin care product (cosmetic) is registered for each cosmetic category (type) in the use cosmetic history database 5d in association with the client ID. Incidentally, the cosmetic which has been purchased by a user is registered in the history data, and the product code of cosmetic (cosmetic being used) which has been purchased by the user via the smartphone 3 is registered. This product code serves as cosmetic specific information with which a cosmetic can be identified. Incidentally, here, an example is illustrated in which the Japanese Article Number (JAN) code, used in a form of a bar code, is used as the product code.

As illustrated in Table 5d1, a number indicating each cosmetic category (type), the product code, a use start date, and a use finish date in the history data are registered in the use cosmetic history database 5d.

Table 5d1 illustrates a case in which the cosmetic category is a facial wash, for example, "1" is registered as a code number of the product category of the facial wash, and the use start date and the use finish date are stored in correlation with the product code. Incidentally, the use finish date is not registered in the case of being in middle of using (case in which the finish of use is not yet input).

In this case, a list of the product names (+the manufacturer names and the like) of the cosmetics corresponding to respective cosmetic categories is displayed by a pull-down menu or the like on the display of the smartphone 3 based on the data registered in the registered cosmetic database 5p in which the cosmetic information is registered, and a cosmetic that the user starts to use may be selected from the list. Accordingly, the product code associated with the cosmetic name of the registered cosmetic database 5p is registered in the use cosmetic history database 5d, and also an input date is registered as the use start date. In the same manner, the user may be instructed to input the use finish date through the dedicated application 5j of the smartphone 3 when there is a cosmetic that the user finished using.

In this case, the user may select the product name or the like of the cosmetic that the user finished using by displaying the list of the data such as the product name of the cosmetic that the user has started to use in a form of the pull-down menu or the like. Even in this case, the product code of the selected cosmetic is input, and also the input date is registered as the use finish date. Incidentally, a method of inputting the used cosmetic may be executed by inputting a bar code or inputting the cosmetic data which is extracted by retrieving the registered cosmetic database 5p through a keyword retrieval.

In addition, in regard to the use finish date, it may be configured such that an inquiry is made to the user whether the use of the cosmetic of the same category, which has already registered, is finished in a case in which a cosmetic of the same category is newly registered in the use cosmetic history database 5d, and the use finish date of the cosmetic is registered based on an answer to the inquiry. Alternatively, it may be configured such that a cosmetic volume (ml) and a recommended use amount (ml/time) is registered for each of the cosmetics in the registered cosmetic database 5p, then a value obtained by multiplying the number of times of using the cosmetic per day by the recommended use amount is summed (accumulated) every day from the use start date in the data management server 5 or the smartphone 3 while being compared with the cosmetic volume, and the user is informed, by the dedicated application 5j, whether the cosmetic being used by the user is running out or whether a residual amount is scarce, and inquired whether the user has finished using the cosmetic, and the use finish date may be registered based on the answer thereto in a case in the which the value summed every day exceeds the volume or exceeds a predetermined proportion, such as 90%, of the volume.

In addition, at this time, a message to encourage the purchase of the cosmetic remaining scarce may be displayed, or a URL of a page of the product remaining scarce in a mail-order site of the cosmetics may be displayed in a link to the page.

In addition, it may be configured such that a different cosmetic of the same category as the cosmetic remaining scarce is displayed for introduction in response to the state in which the cosmetic having been used so far is running out or remaining scarce. At this time, a URL of a web page of the cosmetic of a manufacturer or a sales company of the cosmetic may be displayed in the state of being linked to the page.

As illustrated in Table 5d2 of FIG. 5, examples of the cosmetic category include a facial wash, a makeup remover, lotion, milky lotion, cream, serum, whitening lotion, and others, and the above-described category number is associated with these respective categories. Incidentally, the above-described cosmetic categories are merely examples, and different categorization may be applied.

As illustrated in FIG. 5, the care chart database 5o is configured such, for example, that a cosmetic used by the user in the morning and night every day is arbitrarily registered therein in association with the client ID of the user. The cosmetic used in the morning and night every day can be registered in the care chart database 5o while the use start date and the use finish date of the cosmetic are registered in the above-described use cosmetic history database 5d. The data of the used cosmetic is input and transmitted to the data management server 5 through a scheduler function which will be described later.

Accordingly, the client ID, a date, a time zone such as the morning and night, and the above-described product code as used cosmetic data are registered in the care chart database 5o.

For example, as illustrated in Table 5o1 of FIG. 5, the date and the time zone such as the morning and night, and the product code of the used cosmetic are registered in the care chart database 5o. With this product code, the cosmetics registered in the use cosmetic history database 5d are displayed on a screen of the smartphone, and the actually used cosmetic can be selected from the displayed cosmetics and input.

The measurement data (input skin image, input evaporation meter data, and input melanin meter data) to be input from each of the skin condition measurement devices 1, is registered in the skin history database 5b of the measurement data database 52 illustrated in FIG. 6 in association with the client ID, the data input date and time, and the data No. In addition, each result of the simple diagnosis (analysis) serving as analysis result storage means is registered in association with the measurement data. Incidentally, comprehensive simple diagnosis is executed in a case in which the measurement data is input from a plurality of types of the skin condition measurement devices 1 within a predetermined time scope, for example, 30 minutes or the like, and data of a result of the comprehensive simple analysis is registered. Further, when detailed diagnosis is executed with respect to the measurement data, a result of the detailed analysis is informed, and then, data of the result of the detailed analysis is registered in the detailed diagnosis result database 5e, in association with the client ID and the measurement date and time, and a storage address of the corresponding data written in the detailed diagnosis result database 5e is registered in the skin history database 5b.

Incidentally, the wording of diagnosis in the present specification is not limited to a medical practice, but also includes a non-medical practice, and is used in a broad sense including various types of analysis and the like.

Incidentally, the simple diagnosis is configured such that, for example, measurement data, accumulated in advance, and a rank of the skin condition as the diagnosis result data are preliminarily associated and registered in the skin reference value database 5g, and approximate measurement data is selected from the measurement data in the skin reference value database 5g with respect to the measurement data as the measurement result, and the rank associated with the selected measurement data is output as a result of the simple analysis to the skin reference value database 5g. This process is performed according to a simple diagnosis program 5f of the data management server 5 which serves as skin condition analysis means. In addition, when the measurement data is the image data 22 as in the camera for the skin, the image data 22 serving as the measurement data is binarized, and the skin condition is analyzed based on a pattern of the binarized image data 22 which is recognized according to a well-known image recognition.

Incidentally, as illustrated in Table 5b1, the input skin image includes an image for skin texture diagnosis, which is photographed using the LED illumination of the skin color light, an image for spot diagnosis, which is photographed using the LED illumination of the white color light, and a skin image which is imaged using the LED illumination close to natural light or a skin image having colors reproduced by white balance (for example, automatic white balance) at the time of photographing with the LED of the above-described white color light or skin color light in the case of using the camera for the skin. The skin image is used for determining a skin color (color difference due to suntan, darkening or the like), for example. Incidentally, the determination of the skin color is not performed in the simple diagnosis but is performed in the detailed diagnosis in the present embodiment. It is configured such that each image quality data with respect to the above-described three types of skin images is registered, and the respective smartphones 3 are configured to be capable of responding to the difference in image quality of different cameras.

Incidentally, data for the color correction at each photographing is also registered in the image quality data, and accordingly, it is possible to omit the calibration database 5m in which the data for calibration of the image quality is registered.

The image quality data is configured to correct the difference in image quality caused by the difference of models of the respective smartphones 3 in the case of using the built-in digital cameras of the smartphones 3. For example, the image quality is different depending on the model of the smartphone 3 in a case in which the digital camera 31 built in the smartphone 3 is used for photographing of the image for the skin texture diagnosis, the image for the spot diagnosis, the skin image or the like, and thus, the dedicated application 5*j* is configured to transmit image quality data for each model of the smartphones 3 to the skin history database 5*b*. Here, the image quality data is resolution, for example. The resolution may be, for example, the number of effective pixels of an imaging element, or may be the number of pixels of the photographed image data 22.

In addition, the resolution may be a size and the number of pixels of the imaging element of the digital camera. Each image is converted to the image quality data of an diagnosis and analysis item, set in advance, at the time of diagnosis and analysis, and the diagnosis and analysis is performed. For example, the resolution is increased by interpolation or a super-resolution technology to perform the diagnosis and analysis in a case in which the skin image has low resolution with respect to the image quality data as an object of the skin diagnosis, and the pixels are reduced to decrease the resolution to perform the diagnosis and analysis in the opposite case in which the skin image has high resolution.

In addition, it may be configured such that image quality is determined in advance for each of the image for the skin texture diagnosis, the image for the spot diagnosis, and the skin image regarding the image to be registered in the skin history database 5*b*, and when image is sent from the user, the image is converted to the image quality determined by the dedicated application 5*j* of the smartphone 3 or the program of the data management server 5, and then, is registered in the skin history database 5*b*. In this case, the image quality data is not mandatory as the item of the skin history database 5*b*.

In addition, it is configured such that positional information (measurement point), which is measured by a GPS built in the smartphone 3 according to the data input date and time, is registered as GPS data in the skin history database 5*b*. In addition, it is configured such that weather information (meteorological data) for each measurement point of the above-described GPS is acquired from a weather information site and registered. Incidentally, the data input date and time is a date and time when each measurement of the skin was performed, but may also be a date and time when a result of the simple diagnosis was stored. The data of respective items is automatically input by performing the skin measurement.

A measurement condition flag is configured such that, for example, when the GPS data is distant from a normal measurement point, for example, in a case in which the skin measurement data is input from a measurement point being spaced apart by a predetermined distance or more while measurement has been consecutively performed in the same prefecture or same city in a plurality of times measurement until the preceding measurement, a flag (measurement condition flag) is set on the measurement data measured at the measurement point or the simple diagnosis result Incidentally, the flag may be set on the measurement data or the simple diagnosis result in a case in which temperature and humidity in the weather information exceeds a predetermined range or a difference from an average temperature or an average humidity at the measurement point on the input date and time exceeds a predetermined range, in addition to the measurement point.

When statistical processing, such as obtaining an average of respective data, is executed, the measurement data and or simple diagnosis result on which the flag has been set is excluded, and, for example, the data on which the flag has been set is configured not to be included in a parent population at the time of performing the statistical processing.

That is, there is a possibility that the measurement result becomes an abnormal value in the case of being at a location spaced distantly apart from a usual location, or in a case in which the weather condition is significantly different since the environmental conditions are significantly different, and accordingly, the data on which the flag has been set is excluded from the parent population of the statistical processing in order to prevent the abnormal value from affecting a statistical result.

A score (rank) and a deviation value serving as the simple analysis result on the texture, the spot, and a wrinkle to be obtained as described above are registered in the simple diagnosis result of the skin image (Table 5b2). In addition, a skin type is selected based on the diagnosis results on the texture, spot and wrinkle, a color in the skin image (redness due to dryness or skin roughness, or the like), presence or absence of eczema caused by atopic dermatitis, and disorder of the texture due to dryness. Incidentally, the skin type is also determined by the detailed analysis.

In addition, the detailed diagnosis is performed for the measurement data in servers of cosmetic companies, for example, as affiliated companies (a server 61 of cosmetic company A and a server 61 of cosmetic company B), the servers of the cosmetic companies serve as the skin condition analysis means. Basically, measurement data approximate to the measurement data obtained by the skin condition measurement device 1 is selected from the database included in a detailed diagnosis system 62 in which the measurement data and the analysis result data are correlated, similarly to the simple diagnosis, and the analysis result data associated with the selected measurement data is output. However, in the detailed diagnosis, for example, each number of the registered measurement data and the analysis result data is larger than the case of the simple diagnosis, and is in the state of being classified more in detail into the database for the detailed diagnosis to obtain an analysis result more particular than that in the simple analysis. In addition, it may be configured such that the measurement data registered in the database is selected for the detailed diagnosis with a proprietary algorithm of each of the cosmetic companies to obtain an analysis result corresponding thereto. Incidentally, at the time of the analysis of the image data 22 except for the skin color, binarization is performed with reference to a predetermined threshold, for example, and the skin condition is analyzed according to an area ratio between black and white, each pattern of black and white or the like.

The server of the cosmetic company is provided with a recommended cosmetic determination unit 63, which determines a cosmetic to be recommended to the user based on the result of the above-described detailed diagnosis, and an advice determination unit 64 that determines a method of skin care or content of an advice to give an advice regarding a care appliance or the like which is advantageous for the skin care based on the result of the detailed diagnosis.

The detailed diagnosis result database 5*e* is configured such that the result of the above-described detailed diagnosis is registered therein in association with the client ID, and diagnosis date and time on which the detailed diagnosis is performed (which may include the measurement date and time of the measurement data on which the detailed diagnosis is requested), and the data of the result of the detailed diagnosis are registered therein. In addition, data of the advice and data of the recommended cosmetic (skin care product), which are selected in response to the result of the detailed diagnosis, are registered therein.

Meanwhile, the skin images are acquired by regularly performing photographing in the analysis using the skin image, and accordingly, it is possible to know a change in the skin condition over time in this information management system for surface condition measurement and analysis and the information management method for surface condition measurement and analysis. A method of outputting the photographed image as the moving image or the slide show is effective as a method of displaying the change over time. However, it is necessary to photograph the same range at each photographing in order to realize the above-described method, in the case of nearly regularly photographing the skin by attaching the above-described lens module to the camera for the skin or the digital camera of the smartphone 3, which is difficult.

In a case in which the photographing is performed by attaching the conversion lens to the built-in digital camera of the smartphone 3, for example, it is difficult for the user to directly view the display of the smartphone 3 in the middle of photographing, and it is difficult to specify a position on the skin by viewing the display of the smartphone 3 using a mirror, for example.

That is, there is no characteristic part, which may serve as a reference of the position on the skin, in the skin, and there is a high possibility that it is difficult to determine whether the same location as a location which has been photographed at the previous time is photographed even if the photographing position of the skin is favorable viewable. Although there is a high possibility that it is possible to photograph nearly the same position every time in the case of photographing the spot using the spot as the reference, it is still difficult to photograph the same position every time.

In addition, since the camera for the skin is moved with respect to the smartphone 3 using a USB cable in the case of connecting the camera for the skin to the smartphone 3 using the USB interface 13 or the like, it is possible to determine the photographing position on the skin while directly viewing the display of the smartphone 3, but it is difficult to regularly photograph the same position every time unless there is the characteristic part serving as a clear target as described above. As described above, it is more difficult to photograph the same part in the method of directly attaching the skin lens to the smartphone 3.

In addition, when the photographing position on the skin is greatly deviated in each photographing, it is difficult to understand whether the change in the skin condition is a change due to the passage of time or a change due to the difference in position. In the present embodiment, a photographing point is set, and a relative position of the photographed image data 22 is calculated in the case of sequentially photographing the photographing point so as to enable the grasp of whether a difference in the skin condition on the image is caused by the passage of time or the difference in the position, thereby increasing the accuracy in the analysis of the skin condition, and further, the display is performed based on the relative positions of the respective image data 22 in the case of displaying the image data 22 as the slide show (moving image) in the photographed order such that the same position of the skin is displayed at each point on the screen of the respective slides (frames) as a method of solving the above-described problems. That is, it is configured such that pores (illustrated in FIGS. 9 and 10) 20, which are the same, are displayed at the same position in any slide among the respective slides.

A description will be given as below regarding the overview of a process of calculating the relative positions of the respective photographed image data 22 in a case in which a photographing point of the skin, which serves as the above-described object to be photographed, is determined and a plurality of images are sequentially photographed at the photographing point, and a process of performing the display of the image data 22 based on the relative position.

When the subject is regularly photographed, this information management system for surface condition measurement and analysis is configured such that, first, a photographing point indicating the center of a photographing range on the skin on the image of the entire face is set in a case in which the subject is set to the skin of the face so as to enable the photographing point (a circle that surrounds numerical values as the numbers of photographs on the drawing), for example, as illustrated in display screens 3e, 3f and 3g of the smartphone 3 of FIG. 8, on the image of the entire face to be confirmed at the time of photographing or the like. Incidentally, the face image may be an actual image obtained by photographing the actual face of the user, or may be a drawing which is illustrated based on the actual image. Alternatively, in a case in which the face image is a drawing, it may be configured such that a plurality of types of drawings of the faces are stored in advance, and a drawing to be used can be selected from the plurality of types of drawings of faces.

The photographing point is configured such that a point which is the middle of a line segment connecting two corners of the eyes, for example, of the face image is set to an origin point of the entire face coordinate system, and each position of the photographing points is illustrated in the XY coordinate system or the polar coordinate system. Here, for example, the line segment connecting the corners of the eyes is set as a reference of an angle of the coordinates (angle of deviation) using the polar coordinate system. Incidentally, the entire face coordinate system is configured to display the photographing point on the face image.

When the user sets the photographing point on the above-described face image by touch or the like, the coordinate on the entire face coordinate system is calculated and stored. When the user photographs the determined photographing point, the photographing is performed by designating the photographing point on the entire face coordinate system which is displayed based on the above-described coordinate on the face image.

Accordingly, the user confirms the photographing point on the face image at the time of photographing so that it is possible to suppress the photographed point is set to be a position spaced apart from the photographing point at the time of photographing.

The polar coordinate system having the center position on the image data 22 as the origin point is set in the photographed image data 22, and a position of the pore 20 reflected on the image data 22 is calculated. Incidentally, the origin point may be set to a lower end on the left end of the image in a case in which an image shape of the image data 22 is a rectangle and the Cartesian coordinate system is used.

Each coordinate position of the pores 20 described above of the image data 22, which is photographed for the first time after setting the photographing point, is stored as pore data for comparison with an arrangement pattern of the pores 20 of the image data 22 which is subsequently photographed by designating the same photographing point. When the subsequently photographed image data 22 is input, each coordinate of the pores 20 in the polar coordinate system having the center of the image data 22 as the origin point is calculated in the same manner, and a pore coordinate table in which these coordinates are registered is created.

Incidentally, each of the pore data and the pore coordinate table is a table of the coordinates of the pores 20 having the center of the image data 22 as the origin point in this step, and the pore coordinate table includes the coordinates of the pores 20 of the single image data 22 while the pore data is configured to allow the coordinates of the pores 20 of the image data 22 having the determined center position to be sequentially added and registered.

Basically, there is a high possibility that image data 22 (image having reference numeral 21*a* as the center), photographed for the first time, and the subsequently photographed image data 22 (image having reference numeral 21*b* as the center) have an overlapping part of regions as illustrated in FIG. 9 even if there is a deviation illustrated using an arrow 24. Accordingly, a nearly coincident part is generated in the arrangement patterns of the pores 20 of the two image data 22 to be compared. The part at which the arrangement patterns of the pores 20 coincide with each other is the overlapping part between the two image data 22. In this case, a coordinate system of the photographing points, which sets the image data 22 photographed for the first time as a reference image, and the center of the reference image as the origin point, is set. Incidentally, a description will be given later regarding a case in which there is no part at which the arrangement patterns of the pores 20 do not coin with each other between the image data 22 photographed for the first time and the subsequently photographed image data 22.

The coordinate of the pore 20 of the image data 22 overlapping with the image data 22 as the reference image as above is converted into a coordinate in the above-described photographing point coordinate system, and the coordinate of the pore 20 which does not overlap with the coordinate of the pore 20 that has been registered in the pore data is added in the pore data. In addition, a coordinate (positional coordinate of the image center) at a center position 21*b* of the image data 22 in the photographing point coordinate system is obtained, and the position of the image data 22 is determined. Thereafter, the pore coordinate table is obtained every time the photographed image data 22 is input, and is compared with the pore data, and then, the coordinate of the pore coordinate table is converted as described above and the converted coordinate of the pore 20 is additionally registered in the pore data when there is the part at which the arrangement patterns of the pores 20 coincide with each other, and a coordinate of the center position of the image data 22 in the photographing point coordinate system is determined.

Incidentally, the shape of the image in the image data 22 is set to the circle, but may be set to a rectangle. In addition, there is a possibility that the part having the coincident arrangement pattern of the pores 20 is generated as the coordinate of the pore 20 is additionally registered in the pore data, based on the additionally registered pore data, even in the image data 22 which has been once determined that there is no part having the coincident arrangement pattern of the pores 20 with the pore data in the pore coordinate table, and accordingly, the pore coordinate table of the image data 22 in which the arrangement pattern of the pores 20 coincident with the arrangement pattern of the pores 20 in the pore data was absent and the pore data are compared whenever the coordinate of the pore 20 is additionally registered in the pore data. At this time, if there is a part with the coincident arrangement pattern of the pores 20, the coordinate of the pore 20 of the image data 22 is converted into the coordinate as described above, is additionally registered in the pore data, and further a positional coordinate of a center of the image of the corresponding image data 22 is determined.

In this manner, the relative position of the image data 22 which includes the part having the coincident arrangement pattern of the pores 20 with the pore data is determined in the image data 22 photographed at the same photographing point. That is, the position in the photographing point coordinate system is determined when each of the image data 22 includes a part at which the arrangement of the pores 20 coincide with the arrangement of the pores 20 in the pore data as illustrated in FIG. 10. Accordingly, it is possible to understand the photographing date and time of the respective image data 22 and the positional coordinates of the image centers as the relative positions of the respective image data 22, and it is possible to prevent a case in which skin conditions of clearly different positions are misunderstood as skin conditions at nearly the same position at the time of analyzing the skin condition, and to determine the skin condition with higher accuracy.

When the slide show is displayed, and, for example, in a case in which a rectangular range indicated by reference numeral 26 is set as a position of a display screen that displays the image data 22, it is possible to display the respective image data 22 such that each center of the image thereof is at the corresponding coordinate in the photographing point coordinate system by setting the above-described photographing point coordinate system to the display screen. In this case, the same pore 20 of the different image data 22 is displayed at nearly the same position. In this case, there is a part lacking an image in each slide, but image having been once displayed remains until being overwritten, and accordingly, the preceding image data 22 is displayed in the part lacking the image, and a easily viewable screen is displayed.

In this case, an image is formed as if being fast-forward reproduced after fixing the camera using a tripod or the like and performing a very-low-speed photographing, for example. Incidentally, the part lacking the image of each slide may be interpolated based on the preceding and subsequent image data 22.

Next, a description will be given regarding a relationship between each data, which is used in a process of photographing and reproducing the plurality of images at the same photographing point as described above, and the respective databases. First, a maximum number of photographing points that can be registered for each user (maximum number of registration photographing points) is registered in the client personal information management database 5*a* at the time of joining the membership as illustrated in FIG. 5. Incidentally, the photographing point that can be registered by the user is set to be changed depending on types of membership, for example, free membership, paid membership or the like, and it may be configured such that, for example, the free membership can set only a single photographing point, and the paid membership can set three photographing points. In addition, it may be configured such that different billing is generated depending on the number of the photographing points. The number of the photographing points can be arbitrarily set, and it may be configured such that the number of the photographing points that is available to the user is determined according to various types of condition.

The image data 22 photographed after determining the photographing point is registered in the item (Table 5b1) of the input skin image of in the skin history database 5*b* as illustrated in FIG. 6. Incidentally, the image data 22 includes the image for the skin texture diagnosis, the image for the spot diagnosis, and the skin image, and, for example, the skin image is used although any type of these image data 22 may be used at the time of obtaining the position of the image data 22. Incidentally, the above-described three types of image data 22 including the texture, the spot and the skin is photographed at the time of photographing in the single photographing point, and thus, a position of one type of the image data 22 (a positional coordinate of the center of the image) is determined, a positional coordinate of the center of the image of another type of the image data 22 is also set.

As illustrated in Table 5b1 of FIG. 6, the coordinate of the photographing point in the above-described entire face coordinate system is registered in the item of the input skin image of the skin history database 5b in response to the respective images as the photographing point (center coordinate), and it is possible to retrieve any photographing point being photographed in the respective image data 22.

In addition, each center position of the image data 22, photographed with each photographing point as a target, is configured to be obtained from the relationship with another image data 22 (skin image data) at the same photographing point, and such each center position of the image data 22 is configured to be registered in the item (Table 5b1) of the input skin image of the skin history database 5b as the "positional coordinate of the image center". Accordingly, it is possible to understand the relative positions of the image data 22, which have been sequentially photographed at the same photographing point.

Here, the coordinate system for the "positional coordinate of the image center" is not the entire face coordinate system, but is set to the above-described photographing point coordinate system in which the center of a reference image is set as the origin point when the reference image is determined based on the photographing point. If the polar coordinate is used, it is possible to set the horizontal of the reference image as the reference of angle. In addition, in the case of determining the positions of the respective image data 22, the positions are not necessarily limited to be determined in the photographed order. Thus, it is configured such that a position determination flag is set on for the image data 22 of which the positional coordinate of the center of the image is determined, and the position determination flag remains in the state of being turned off in the image data 22 of which the positional coordinate of the center of the image is not yet determined. This position determination flag is registered in the item of the input skin image of the skin history database 5b (Table 5b1). Incidentally, there are not only vertical and horizontal positional deviations but also a positional deviation in the rotation direction in the image data 22 obtained by photographing the same photographing point, the horizontal in the reference image basically serves as the reference of the angle (angle of deviation) of the coordinate, and the angle of the image data 22 is determined for the other image data 22 based on a region with the arrangement pattern of the pores 20 coincident with the pore data.

The registered number of the photographing point (the number of registered photographing point) is stored in the photographing point database 5c in association with the client ID. This registered number of the photographing point is not the above-described maximum value, but is the number of the photographing points that have been already registered by the user within the range of the maximum value, and is an arbitrary value from 0 to the maximum value.

The center coordinate of the photographing point is registered as the coordinate of the entire face coordinate system in the photographing point database 5c in response to each registered photographing point in association with the client ID.

In addition, the number of the registered (photographed) image data, the date on which the photographing point was registered, the data No. of the reference image, and the above-described pore data are registered in the photographing point database 5c in association with the center coordinate of the photographing point (the entire face coordinate system). The data No. of the reference image is a data No. of the image data 22 which is set as the reference image among the data Nos. being assigned for each of the image data 22 as the respective measurement data at the time of measuring the respective measurement data, and registered in the skin history database 5b.

The pore data is the same coordinate table as the pore coordinate table, and the coordinate, which indicates each position of the pores 20 of the respective image data 22 in the photographing point coordinate system of the photographing point, is registered using a moving radius (rn) and an angle of deviation (θn) of the polar coordinate as illustrated in Table 5b4 of FIG. 6. Incidentally, the coordinates are registered such that the pores 20 having the coincident arrangement pattern among the image data 22 are regarded as the same pore 20 as described above.

Next, a description will be given regarding a process of adding and changing the registration photographing point relating to the registration of the photographing point with reference to the flow charts of FIGS. 7, 8 and 12. The process of adding and changing the registration photographing point is a process to be performed by the smartphone 3, the center coordinate of the photographing point, added or changed based on the process of adding and changing the registration photographing point in the smartphone 3, is transmitted to the data management server 5, and the data management server 5 allows the added or changed center coordinate of the photographing point to be newly registered in the photographing point database 5c. Incidentally, addition of the photographing point and erase of the photographing point are combinedly performed in the change of the photographing point, and accordingly, the added photographing point is registered in place of the erased photographing point.

As illustrated in FIG. 7, when the dedicated application 5j is activated to display the main menu illustrated in the display screen 3a in the smartphone 3, it is possible to select the esthetic diagnosis as a choice for performing the measurement using the skin condition measurement device 1 among choices. The esthetic diagnosis is selected to display the esthetic diagnosis menu illustrated in the display screen 3b. The skin diagnosis using the skin condition measurement device 1 can be selected in the esthetic diagnosis menu, the skin diagnosis menu illustrated in the display screen 3c is displayed when the skin diagnosis is selected, a skin diagnosing camera (the camera for the skin) can be selected as the skin condition measurement device 1, and a photographing type menu illustrated in the display screen 3d of FIG. 8 is displayed when the skin diagnosing camera is selected so that the type of photographing can be selected.

Here, there are two types of photographing, and it is configured such that either a continuous skin photographing or a pinpoint photographing can be selected. In the continuous skin photographing, a photographing point is set on the skin, and the set photographing point is regularly photographed. In addition, the continuous photographing is not performed in the pinpoint photographing, and the user receives the simple diagnosis based on photographed skin image. Incidentally, the simple diagnosis is performed also in the case of the continuous skin photographing. In the pinpoint photographing, an area of concern in the skin is photographed on trial to receive the simple diagnosis. In addition, it is available in the case of making an acquaintance of the user receive the simple diagnosis of the skin on trial.

In the smartphone 3, it is determined whether the continuous skin photographing is selected from the photographing type menu. (Step S1).

When the pinpoint photographing is selected without selecting the continuous skin photographing, then, the skin is photographed by the camera for the skin, the photographed image data 22 is transmitted to the data management server 5, and the simple diagnosis is performed using the image data 22.

In the case of selecting the continuous skin photographing, the data of the photographing point database 5c is downloaded from the data management server 5, and when there is a photographing point which has been already registered in the photographing point database 5c, the photographing point, the registration date of the photographing point, and the number of photographs at the photographing point, and further an addition and change button of the registration photographing point are displayed on the face image, as illustrated in the display screen 3e of FIG. 8, based on the registered center coordinate of the photographing point of the photographing point database 5c, the number of images photographed at the corresponding photographing point, and the registration date of the photographing point. That is, the display screen 3e is created and displayed (Step S2). Incidentally, when the photographing point has not been registered, a face image with absence of the photographing point is displayed, but it may be configured to move to Step S5.

Incidentally, the polar coordinate system (the entire face coordinate system) in which the point in the middle of the line segment connecting the two corners of eyes is set as the origin point, is set on the face image as described above, and the polar coordinate in the entire face coordinate system is stored, as the photographing point, in the photographing point database 5c.

It is determined whether one of the displayed photographing points is touched (Step S3).

In a case in which the displayed photographing point is not touched, it is determined whether the addition and change button of the registration photographing point is touched (Step S4).

In a case in which the displayed photographing point is touched, this process is ended, and the display screen 3g of FIG. 8 is displayed. Only the photographing point that is touched is displayed on the face image in the display screen 3g, and the user is encouraged to photograph this photographing point, and the processing is shifted to a photographing process. In a case in which the addition and change button of the registration photographing point is touched, the display screen 3f of FIG. 8 is displayed (Step S5).

In the display screen 3f, a display to encourage input of a new photographing point is displayed on an image basically the same as the display screen 3e. It is determined whether the user touches the face image on the display screen 3e as the input of the new photographing point (Step S6).

In the case of being touched, the above-described position of the coordinate system (the entire face coordinate system) on the face image at the touched position is obtained (Step S7).

In addition, it is determined whether the registered number of the photographing points at the current situation is a set upper limit value, for example, 3 (Step S8), and when the registered number is smaller than 3, that is, it is possible to newly register a photographing point, an item of a new photographing point is set in the downloaded photographing point database 5c, a center coordinate of the photographing point and a date of the current date serving as the registration date are registered with the item of the photographing point, and the number of the photographed skin images is set to 0 (Step S9).

In addition, the rewritten photographing point database 5c is transmitted to the data management server 5, further, the display screen 3e is created based on the rewritten photographing point database 5c and displayed (Step S10), and the processing returns to Step S3. Incidentally, the photographing point database 5c is updated to be replaced by the received photographing point database 5c in the data management server 5.

When the registered number of the photographing points at the current situation is the upper limit value, it is not allowed to newly increase the photographing point, and thus, a display screen, which allows the user to input whether to instruct a photographing point to be deleted or to cancel the input of the photographing point, is displayed (Step S11).

The user touches a cancel button which is displayed on the same display screen as the display screen 3f or gives an instruction by touching the photographing point to be deleted.

It is determined whether the photographing point to be deleted is touched in the smartphone 3 (Step S12).

In a case in which the photographing point is not touched, it is determined whether the cancel button is touched (Step S13).

In a case in which the cancel button is touched, the original display screen 3e on which a new photographing point is not displayed is displayed, and the process returns to Step S3.

In a case in which the photographing point is touched, data of an item of the touched photographing point is deleted from the photographing point database 5c, downloaded from the data management server 5, based on a coordinate of the touched photographing point and the number of the photographing points, for example, 1 to 3 (Step S14), the process is shifted to Step S9, and the precedently touched point is registered as a new photographing point in the photographing point database 5c as described above, and is transmitted to the data management server 5.

In this process, in a case in which a photographing point to be photographed at the current time is finally touched in Step S3, the process is ended as described above and the process is shifted to the photographing process.

In the photographing process, for example, the photographing of the skin texture, the photographing of the skin spot, and the photographing of the skin color described above are performed, and the photographed image data 22 is transmitted from the smartphone 3 to the data management server 5.

At this time, not only the respective photographed image data 22 (the skin texture diagnosis image, the spot diagnosis image and the skin image) but also the client ID, the data input date and time (the photographing date and time), the GPS data (the measurement point), the image quality data of the respective image data 22 (for example, the resolution of the camera used in the photographing), the coordinate of the photographing point, and the position determination flag (off) are transmitted from the smartphone 3 to the data management server 5.

In the data management server 5 that receives these data, these data is registered in the skin history database 5b in association with the client ID. Incidentally, the positional coordinate of the center of the image is not determined and registered at this time. The position determination flag remains in the off-state. In addition, the simple diagnosis process is performed based on the respective image data 22, and the simple diagnosis result is transmitted to the smartphone 3 to be displayed on the display of the smartphone 3. In addition, the simple diagnosis result is registered in a skin image simple diagnosis result of the skin history database 5b.

As the simple diagnosis result is displayed after the photographing of the skin, a state is formed in the smartphone 3 in which a series of processing is ended, and then, the process is shifted to a display screen of a different item of the dedicated application 5j or the dedicated application 5j is ended in a state in which the simple diagnosis result is displayed using the dedicated application 5j, for example.

Meanwhile, when the image data 22 is registered based on the continuous skin photographing, a process of determining a positional coordinate of the center of an image is performed in the data management server 5 after ending the transmission of the simple diagnosis result to the smartphone 3 described above.

Hereinafter, a description will be given regarding the process of determining the positional coordinate of the center of the image to be performed in the data management server 5 with reference to flowcharts illustrated in FIGS. 13 and 14.

The position of the pore 20 is analyzed through the image recognition using the image data 22 of the skin (the texture, the spot and the color), which is transmitted from the smartphone 3 and registered on the item of the input skin image of the skin history database 5b (Table 5b1) as described above, the coordinates of the respective pores 20 in the polar coordinate system having the center of the image of the image data 22 as the origin point, for example, and the pore coordinate table in which these coordinates of the pores 20 are registered is created (Step S21).

For example, the photographed image data 22 is transmitted from the smartphone 3 to the data management server 5, and the simple diagnosis is performed using the received image data 22 in the data management server 5. Thereafter, the position of the pore 20 on the image data 22 is detected. The detection of the position of the pore 20 is performed by detecting hair (downy hair) on the skin which is easily recognized from the pore 20. Regarding end portions of the recognized hair, a distal end side is thin and base end side, which is the pore 20 side, is thick.

Thus, it is configured such that the end portion on the thick side of the recognized hair is recognized as the pore 20. Incidentally, the recognition of the pore 20 of a normally closed state is difficult in a state in which there is no hair, and thus, here, the base end portion of the hair of the pore 20 having hair is recognized as the pore 20.

Incidentally, the pore 20 of an opened state is easily recognized even if there is no hair as compared to the closed pore 20, and it may be configured such that the opened pore 20 is recognized (only the pore 20 that can be recognized is recognized), and a position on a coordinate is determined in the same manner as the pore 20 having the hair. Incidentally, the arrangement of the pores 20 on the skin is nearly orderly, and has a risk that it is difficult to function as a characteristic point on the image in a case in which the entire pore 20 is recognized and the position thereof is stored, but a difference in the arrangement pattern of the pores 20 is easily caused by recognizing only the pores 20 having the hair and the opened pores 20, and it becomes easy to specify the overlapping part among the respective skin images from the pattern of the pores 20. It may be configured such that the center of a part having a size with equal to or smaller than a predetermined diameter and partial pigmentation (part having color being darken with respect to the surrounding color) is recognized as the pore 20. In addition, there is a case in which melanin is retained in the pore 20 part so that a small spot is caused, and it may be configured such that such a spot of equal to or smaller than a predetermined size is recognized as the pore 20.

Next, it is determined whether photographing at the selected photographing point is performed for the first time (Step S22). That is, it is determined whether the number of images at the selected photographing point in the photographing point database 5c is one.

In the case of the first photographing, the pore coordinate table is registered in pore data of the corresponding photographing point in the photographing point database 5c (Step S23). At this time, the position determination flag remains in the off-state. The pore data is a coordinate table of the pore 20 to be used for specifying each position of the respective image data 22. The coordinates of the respective pores 20 in the pore data are coordinates in the above-described photographing point coordinate system in which the center position of the reference image is set to the origin point. Here, however, the reference image is not determined, and the state without image data 22 of which the position is determined is formed, and accordingly, the pore coordinate table in which the coordinate of the pore 20 in a coordinate system having the center of the image data 22 of the first photographing as the origin point is registered is assumed to be the pore data, and is registered in the corresponding photographing point in the photographing point database 5c. In the case of the first photographing, the pore coordinate table to be compared with the pore data is not present, and thus, the process is ended.

In a case in which it is determined not to be the first photographing at the selected photographing point in Step S22, that is, a case in which the number of images at the selected photographing point in the photographing point database 5c is two or more, it is determined whether the part at which the arrangement pattern of the pores 20 of the created pore coordinate table and the arrangement pattern of the pores 20 of the pore data coincide with each other is present (Step S24). At this time, it is determined whether the part with the nearly coincident arrangement pattern of the pores 20 is present between the two image data 22 according to a predetermined image recognition algorithm.

For example, it is determined whether there is a part having an analogous arrangement pattern of the pores 20 between the pore data and the pore coordinate table, and it is determined that the two image data 22 have a part in which the same range on the skin is photographed (the part at which the skin images overlap each other (the same part)). Such determination is performed on consideration of a change of the pore coordinate caused by a bulge in the skin surface based on a difference in pressing force of the skin camera to the skin, a change of the pore 20 that can be recognized due to a difference in the photographed environment, or the like, and the presence of the same arrangement pattern is determined with a coincidence ratio equal to or higher than an acceptable value.

Next, it is determined whether a region having the coincident arrangement pattern of the pores 20 between the compared pore data and the pore coordinate table is present (Step S25). If there is no region having the coincident arrangement pattern of the pores 20 between the pore data and the pore coordinate table is present, it is determined whether the reference image has been already determined (Step S26). At this time, the determination is performed with reference to the item of the reference image of the photographing point in the photographing point database 5c, but it may be determined whether the image data 22 having the position determination flag in the on-state is present in the image data 22 corresponding to the photographing point. In a case in which the reference image has not been determined, the process is shifted to Step S23, and the created pore coordinate table is registered, as the pore data, in the photographing point database 5c. At this time, the previous pore data is deleted, and the pore data is updated and stored.

That is, the created pore coordinate table is updated and stored as the pore data every time the image data 22 is received until finding the region having the coincident pore pattern between the pore data, which is the pore coordinate data of the precedently photographed image data 22, and the pore coordinate data of the subsequently photographed image data 22. At this time, since the relative positions of the respective image data 22 have not been determined yet, the process is ended while leaving the corresponding position determination flag in the off-state.

In a case in which it is determined that the reference image has been already determined in Step S26, the process is shifted to Step S33 while leaving the position determination flag of the item of the input skin image of the skin history database 5b, which corresponds to this image data 22, in the off-state (Step S27), and the process is shifted to a process of determining a position of an undefined image.

In a case in which there is the region having the coincident arrangement pattern of the pores 20 between the compared pore data and the pore coordinate table in Step S25, it is determined whether the reference image has been already determined (Step S28). This determination method is the same as described above. In a case in which the reference image data 22 has not been determined, the (N−1)-th image data 22, which is received prior to the N-th image data at the photographing point received at the current time and with which the pore coordinate data is created, and in which the pore data is registered is set as the reference image, and the item of the reference image of the photographing point in the photographing point database 5c corresponding to the data No., which corresponds to the (N−1)-th image at the corresponding photographing point, is registered. (Step S29). At this time, a position determination flag of the (N−1)-th image data 22, which has been photographed at one time earlier, is turned on, and the origin point of the photographing point coordinate system as the coordinate system of the coordinate of the pore 20 to be used in the pore data is determined as the center of the image of the image data 22 determined as the reference image.

Incidentally, the pore data to be stored at this time is the same data as the coordinate of the coordinate system in the pore coordinate table having the center of the (N−1)-th image data 22 as the origin point, and the pore data remains in the same state.

In a case in which it is determined that the reference image is determined in Step S28, or the process of Step S29 is performed, a coordinate of the center of the image of the N-th image data 22, which is the photographed image at the current time and has the region in which the pore data and the arrangement pattern of the pores 20 coincide with each other, is converted into a coordinate in the photographing point coordinate system. The coordinate of the center of the image of the N-th image data 22 in the photographing point coordinate system is registered in the input skin image (Table 5b1) of the skin history database 5b. Further, a position determination flag of the input skin image (Table 5b1) of the skin history database 5b is turned on (Step S30). Accordingly, positions of the texture, the spot and the skin in the photographing point coordinate system of the center of the image of the N-th image data 22 are determined.

Next, the coordinates of the respective pores 20 of the N-th image data 22 in which the center of the image is determined as above are converted into a coordinate system having a diameter of the photographing point coordinates (in which the center of the reference image is set as the origin point) (Step S31). That is, the center of the image of the image data 22, which is the origin point of the coordinate system of the coordinate of the created pore coordinate table, is subjected to the coordinate conversion to be the coordinate of the center of the image in the photographing point coordinate system. Accordingly, the coordinates of the respective pores 20 on the image data 22 becomes the coordinate in the photographing point coordinate system which is the same as the coordinate of the pore 20 in the pore data.

Next, the coordinate of the pore 20 of the N-th image data 22, which has been converted into the coordinate of the photographing point coordinate system as described above, is additionally registered in the pore data (Step S32). At this time, the coordinates of the pores 20, which have the coincident arrangement pattern with the pores 20 of the pore data as described above, have been already registered in the pore data, and thus, the coordinates of the pores 20 with the arrangement pattern being not coincident is additionally registered in the pore data.

Next, the process of determining the position of the undefined image (processing in Step S33 and the subsequent steps) is performed. The entire image data 22 in which the position determination flag of the input skin image (Table 5b1) of the skin history database 5b is in the off-state is selected (Step S33). Next, the following processing is executed on the respective image data having the selected position determination flag in the off-state. This processing is executed as loop processing for each image data with the position determination flag in the off-state, and the same processing is executed on the image data, one by one, with the position determination flag in the off-sate.

Here, the number of the image data with the position determination flag in the off-state is set to n, and the processing is executed respectively to first to n-th image data. In addition, "i=1 to n" is set, and the loop processing of sequentially processing the i-th image data is started (Step S34). Incidentally, the processing is ended in a case in which there is no image data with the position determination flag in the off-state.

A pore coordinate table corresponding to the i-th image data 22 among the selected image data 22 is created, and is compared with the pore data of the same photographing point which has been recorded in the photographing point database 5c (Step S35). Here, the coordinates of the pores 20 in the pore data increase due to the above-described additional registration of the pore data, and a possibility of the presence of the region in which the pore data and the arrangement pattern of the pores 20 coincide with each other is generated even in the pore coordinate table of the image data in which the region in which the pore data and the arrangement pattern of the pores 20 coincide with each other has not been present so far.

As a result of the comparison, it is determined whether the pore coordinate table with the region, which has the coincident arrangement pattern of the pores 20 with the pore data, is present (whether the arrangement patterns of the pores are partially coincides with each other) (Step S36), and the coordinate in the photographing point coordinate system of the center of the image of the image data 22 corresponding the pore coordinate table is obtained and is registered in the skin history database 5b in the case of the presence of the region, and further, the position determination flag of the skin history database 5b is turned off (Step S37).

Next, the coordinate table of the pores of the i-th image data is converted into the coordinate system of the reference image, that is, the photographing point coordinate system. That is, the coordinate table of the pores of the i-th image data is converted into the same coordinate system as the coordinates of the positions of the respective pores in the pore data (Step S38). The converted coordinate of the pore coordinate table of the i-th image data 22 is additionally registered in the pore data of the item of the corresponding photographing point in the photographing point database 5c (Step S39). The loop processing started from Step S34 is repeated by adding one to i (Step S40). However, the processing is ended in a case in which i=n, and the processes from Step S35 to Step S39 have been executed.

Incidentally, this processing is executed not in the smartphone 3 but on the data management server 5 side, and thus, can be executed in the background separately from the processing on the smartphone side. Accordingly, it may be configured such that the pore coordinate table corresponding to the entire image data 22, which has been already stored and the position thereof has not been determined, and the pore coordinate table of the image data 22 that has been newly input are compared every time the photographed image data 22 is input via the smartphone 3 of the user until the two or more image data 22 with the regions overlapping each other is found.

In a case in which the image data 22 having the parts overlapping each other is found based on the pore data as above, it is possible to display the pores 20 on these image data 22 at the positions on the same coordinate system. The above-described photographing point coordinate system is used as the coordinate system, and the position at image center of each image is determined as the coordinate. In addition, the coordinate of the pore 20 is converted and unified into the coordinate of the photographing point coordinate system, and is registered in the pore data. Such coordinate conversion is performed on consideration of the change of the pore coordinate caused by the bulge in the skin surface based on the difference in pressing force of the skin camera to the skin. To be specific, a process of multiplying a magnification and a moving radius r is performed in the polar coordinate, for example, while assuming that image is enlarged and contracted using the center of the image as the reference.

In the image data 22 whose relative positions to each other are specified as above, it is possible to grasp the difference of the skin condition caused by the difference of the position. For example, in the case of the image data 22 without the position information, there is a risk of generating the image data 22 in which partial skin roughening is reflected, and the image data 22 in which the skin roughening is not reflected due to the positional deviation.

In this case, there is a possibility that image data 22 seems that the skin roughening is suddenly generated or the skin roughening is suddenly cured, and a state is formed in which it is extremely difficult to understand the change in the skin condition over time.

In contrast, it is possible to grasp the difference of the position in the skin represented by the respective image data 22 in the present embodiment, and thus, it is possible to observe a change in the skin roughening over time only with the image data 22 in which the skin roughening is reflected in a case in which the skin roughening is reflected only in some of the image data 22, for example. Accordingly, it is possible to reduce a mistake to determine that the skin roughening becomes favorable only by viewing the image data 22 in which the skin roughening is not reflected. That is, it is possible to determine the change in the skin condition over time with higher accuracy.

In this case, it is possible to provide data that can be easily used by the partner company when the data is provided to a computer system of the partner company such as the cosmetic company serving as the contractor client 6, and it is possible to provide the data that the partner company wants to have. Accordingly, there is a possibility of increasing the number of contracts as the partner companies or increasing the use amount of paid data.

In addition, it is possible to analyze a result, in detail, obtained by observing the skin condition for a long period to some extent, without using the display in which the disappear and generation of the skin roughening is likely to repeat, in the case of performing the detailed diagnosis of the image data 22, and the more detailed skin diagnosis becomes possible.

In addition, it is possible to display the image data 22, which is registered as the history for the period, on the display of the smartphone 3, and in this case, the display is also performed such that the photographing point coordinate system is set on the display screen, and the coordinate positions of the centers of the images of the respective image data 22 become the coordinate positions of the center of the image registered in the skin history database 5b on this coordinate system.

Next, a description will be given regarding a process of displaying the skin image configured to display the above-described image data 22 on the display screen of the smartphone 3 with reference to a flowchart of FIG. 15 and FIG. 10.

In FIG. 10, the image data 22 to be displayed is displayed on the coordinates of the photographing point coordinate system. That is, a state is formed in which the respective image data 22 is arranged on the photographing point coordinates based on the coordinates of the centers of the images of the image data 22 with the position determination flag in the on-state. The image data 22 with the position determination flag in the off-state is not displayed. The respective image data 22 is displayed as the slide show in the registered order, and a part in a screen display target range (a display range 26: corresponding to the display of the smartphone 3), set on the photographing point coordinate system as illustrated in FIG. 10, of the image data 22 to be displayed is displayed.

In other words, when the display range 26 is set on the photographing point coordinates, it is possible to express a position of each pixel in the display range 26 as a coordinate of the photographing point coordinate, and a state is formed in which the photographing point coordinate is set on the display range 26.

The image data 22 to be arranged within the display range 26 is displayed as the slide show in the registered order corresponding to the coordinate positions of the center of the image.

At this time, the photographing point to display the image data 22, a period of registration dates of the image data 22 to be displayed among the entire image data 22, and a display interval among the image data 22 at the time of being displayed as the slide show are input (Step S41) as illustrated in the flowchart of FIG. 15. For example, in a case in which there are three photographing points, one photographing point thereof is selected and input. In addition, the period of registration dates of the image data 22 to be displayed is input like "January first of last year to January first of this year", or "a year until today". Accordingly, the image data 22 registered in designated period becomes a display object.

In addition, the display interval of the slide show is an interval between display of the preceding image data 22 and display of the subsequent image data 22 at the time of sequentially displaying the respective image data 22, and the display such as the moving image is performed when the interval is shortened.

The display range 26 serving as the screen display target range (coordinate) is determined from the image data 22 serving as an object to be displayed (Step S42). For example, the display range 26 is set based on the coordinate positions of the centers of the images of the image data 22 with the determined position as the image data 22 serving as the object to be displayed. In this case, a range in which the centers of the images are congested the most, and a range including a part at which the image data 22 overlap each other the most are set as the display range 26. Incidentally, it may be configured such that the display magnification of the respective image data 22 in the display range 26 can be set.

Next, the image data 22 is overwritten and displayed in the registered order such that the centers of the images of the respective image data 22 are arranged on the coordinates of the centers of the images on the photographing point coordinates (Step S43).

Incidentally, the image data 22 is displayed although the center of the image does not enter the display range 26 as long as a partial region thereof overlaps with the display range 26. Incidentally, this processing is executed in the smartphone 3, for example, but it may be configured such that the input process of Step S41 is performed in the smartphone 3, then the input data is sent to the data management server 5 to create data for display within the display range 26 in the data management server 5, and thereafter, the created display data is transmitted to the smartphone 3 to display the display data on the smartphone 3.

In this case, the image data 22 is displayed in the photographed order (in the registered order) based on the relative positions on the photographed actual skin. Accordingly, the image data 22 at the same coordinate position (relative coordinate) on the skin is basically displayed at the same coordinate position on the display screen, and a state in which moles vertically and horizontally move around the screen, for example, is not formed during the display, and the moles are displayed in the state of being nearly still at the nearly same positions on the display screen. Accordingly, there is a risk that some of old images are left and displayed without responding to the passage of time, but the change in the skin condition is viewed fast-forward.

FIG. 18 illustrates the display screen of the smartphone 3 in the middle of displaying the sin image on the display screen of the smartphone 3 in a time-series manner based on the above-described flowchart of FIG. 15. In FIG. 18, a display region for the skin image is present in the display screen and a display region for the date and time and the score is present on an upper part thereof. The photographing date and time corresponding to the image data which is overwritten in the display region of the skin image, and a texture score or a spot score of the skin image simple diagnosis result are displayed in the display region for the date and time and the score.

Next, a description will be given regarding a method of processing display of the other image data 22 with reference to flowcharts of FIGS. 16 and 17 and FIGS. 11(a) and 11(b). In the above-described display processing method, the image data 22 is displayed as the respective slides (frames), while the part other than the image data 22 of each slide is displayed without being overwritten on the preceding slide. That is, the part other than the image data 22 in each slide is handled in a transparent state, and the preceding display is left and displayed without being overwritten in the part in which the image data 22 is not present in a single slide.

In contrast, in this display method, the image data 22 is arranged in the region with the image data 22 in the respective slides, and the image data 22 is created through interpolation from the preceding and subsequent image data 22 and is arranged in the region without image data 22. Accordingly, the respective slides include the image data 22 and the interpolated image data in this case.

In the display processing, Step S51 is executed in the same manner as Step S41 described above, and Step S52 is executed in the same manner as Step S42 described above. Next, screen data as the slide (frame) to be displayed on the display of the smartphone 3 in response to the image data 22 with a certain position determined within the input period of the registration date is created from the corresponding image data and the image data interpolated using the preceding and subsequent image data thereof (Step S53). Incidentally, a process of creating the screen data will be described later.

Next, the screen data which is created at the input display interval described above is displayed in the order of old registration date of the image data included in the screen data (Step S54). In this case, there is no risk that the old image data is indefinitely displayed as in the above-described display processing, and the part without image data is not present in the respective slides to be displayed on the display screen, and thus, the slide show (display of the moving image) become easily viewable. Incidentally, the display processing is executed in the smartphone 3, but the process of creating the screen data is performed in the data management server 5, and the created screen data is transmitted to the smartphone 3.

As illustrated in the flowchart of FIG. 17 and FIGS. 11(a) and 11(b), the non-photographed region in which the image data 22 of the screen data 41 is not present is recognized and determined at the time of creating the N-th screen data 41 including the N-th image data 22 (Step S61). Actually, the image data 22 is arranged in response to the coordinate of the center position on the slide (the screen data 41) in which the photographing point coordinate is set, and a region other than the arranged image data 22 is set as a non-photographed region. Incidentally, here, the (N−1)-th screen data 40 is set to have been already created. Incidentally, a method of creating the (N−1)-th screen data 40 is the same as the method of creating the N-th screen data, and screen data 40, 41 and 42 are sequentially created based on the image data 22 in the registered order of the image data 22.

Next, the (N−1)-th screen data 40, which has been already created, and image data 22b and 22c overlapping with the non-photographed region among the (N+1)-th and subsequent image data 22 are used at the time of interpolating the non-photographed region without the N-th image data 22a among the screen data 41. Incidentally, here, the image data 22b and 22c are, for example, the (N+1)-th image data 22b and the (N+2)-th image data 22c, but may be the image data 22 subsequent thereto. That is, the interpolation processing using the N-th screen data 41 is performed from the (N−1)-th screen data 40 and the image data 22b and 22c overlapping with the non-photographed region among the (N+1)-th and subsequent image data 22 to create an image in the non-photographed region (Step S62), and the N-th screen data 41 is created by synthesizing the N-th image data 22a and the interpolated image data 22 (Step S63). Incidentally, it is possible to use a well-known algorithm in the interpolation processing.

The (N+1)-th screen data 42 is created after the N-th screen data 41 is created, and thus, the (N+1)-th time is set to the N-th time (Step S64), and the process returns to Step S61 when the image data 22 which has not been yet processed is present (Step S65). Incidentally the process of creating the screen data 40, 41 and 42 is ended when the screen data 40, 41 and 42 corresponding to the registered image data 22 are created in the selected period as described above.

Even in this display processing method, it may be configured such that the display region of the skin image is provided in the display screen of the smartphone 3 and the display region for the date and time and the score is provided in the upper part thereof, as illustrated in FIG. 18, and the photographing date and time corresponding to the image data which is overwritten in the display region of the image data corresponding to the screen data in the middle of being displayed, and the texture score or the spot score of the skin image simple diagnosis result are displayed in the display region of the skin image.

Incidentally, although the coordinate position of the pore 20 is used as the characteristic part on the image recognition of the parts with overlapping positions on the skin of the image data 22 in the present embodiment, the shape of the pore 20 may be additionally used as a characteristic on the image recognition. For example, it may be configured such that a shape of the pore 20 such as the area of the pore 20 or a diameter of the pore 20 is set as a characteristic part and pores are divided into the large pore 20 and the small pore 20, for example, at the time of observing the arrangement of the pores 20, and it is recognized as the positions do not coincide with each other in a case in which the positions coincide with each other between the small pore 20 and the large pore 20. Accordingly, it is possible to reduce the proportion of being erroneously recognized as the overlap due to the similarity in the arrangement pattern of the pores 20 even when the positions on the skin do not actually overlap each other.

In addition, the shape of the spot may be used as a characteristic part on the image recognition in order to find of the overlapping region between the image data 22. In this case, it may be configured such that, for example, a threshold is determined in the image data 22 of the spot, a state in which the shape of the spot is easily recognizable is formed through binarization into a part with light color and a part with dark color, that is, a state in which the shape of the spot is extracted is form, shapes of the parts with light color or of the parts with dark color are compared in the two image data 22, it is determined that the coincident region is present in a case in which the parts having the approximate shape are present, and relative positions of the two image data 22 are determined.

In addition, in the case of photographing the spot image, the skin texture image and the skin image in the state of arranging the skin camera at the same position on the skin, and in a case in which the positional coordinate of the center of the image of the image data 22 is obtained from the arrangement of the pores 20 using the skin image, the positional coordinate of the center of the image may be applied to the skin texture image or the spot image which is photographed at the same position as the skin image. In addition, the positional coordinate of the center of the image of the image data 22 may be obtained from the arrangement of the pores 20 using the skin texture image or the spot image. In addition, similarly, in the case of obtaining the positional coordinate of the center of the image of the spot image using the shape of the spot as the characteristic part of the image recognition, this positional coordinate of the center of the image may be applied to the skin texture image or the skin image that is photographed at the same position as the spot image. Although the wordings, the "simple diagnosis" and the "detailed diagnosis" is used in this specification, these wording are not limited to the diagnosis conducted by a doctor, but the concept thereof also includes the determination in a broad sense.

REFERENCE SIGNS LIST

1 skin condition measurement device (camera for the skin, smartphone+lens module: skin photographing means)
3 smartphone (skin image display means)
5 data management server
5b skin history database (skin image storage means)
5k control unit (overlap detection means, position determination means)
20 pore
22 image data

The invention claimed is:
1. An information management system for measurement and analysis of a surface condition, the system comprising:
  a photographing means that photographs a surface serving as an object to be measured without fixing a photographing position and generates image data;
  an image storage means that stores the image data and a photographing date of the image data;
  a position determination means that compares a plurality of the image data stored in the image storage means, and determines relative positions of the plurality of image data in a single coordinate system when the plurality of image data, obtained from a plurality of times of photographing performed at an interval using the photographing means, of which photographing positions on the surface serving as the object to be photographed are deviated are stored in the image storage means,
  wherein a center of the respective image data of which the relative positions in the coordinate system are determined is arranged and displayed while deviating from the relative positions in the coordinate system in an order of the photographing date; and
  an image display means that displays the image data stored in the image storage means in the order of the photographing date of the image data.
2. The information management system according to claim 1, wherein the image display means arranges the respective image data of which the coordinate system is set on a display screen and the positions in the coordinate system are determined at the positions of the coordinate system, and displays the image data in the order of the photographing date.

3. The information management system according to claim 2, wherein the image display means displays the image data on a frontmost surface in the order of the photographing date to be held in a state of displaying a part of the image data to be displayed on the frontmost surface, which is displayed prior to relevant image data, that does not overlap with the relevant image data to be displayed on the frontmost surface.

4. The information management system according to claim 2, wherein the image display means generates image data interpolated from the image data having the preceding or subsequent photographing date at time of displaying the image data in the order of the photographing date when a display range to display relevant image data includes a part in which displayed relevant image data is present and a part in which the relevant image data is absent, and the image data having the preceding or subsequent photographing date than the displayed relevant image data is present in the part in which the relevant image data is absent, and displays the interpolated image data in the part of the display range in which the displayed image data is absent.

5. The information management system according to claim 1, wherein when a nearly coincident image region is present between the image data to be compared with each other, the position determination means determines relative positions of the plurality of image data in the single coordinate system based on the image region.

6. The information management system according to claim 5, further comprising:

an overlap detection means that compares the image data being sequentially stored in the image storage means, and determines whether the image regions nearly coinciding with each other are present in the image data, wherein the position determination means sets the coordinate system having one of the image data as a reference when the image regions nearly coinciding with each other are present, and determines a position in the coordinate system of another image data in a state in which the image region that nearly coincides with the one image is superposed, the overlap detection means compares the image data of which the position of the coordinate system is already determined by the position determination means, and the image data of which the position of the coordinate system is not yet determined, and determines whether the image regions nearly coinciding with each other is present, and when the image data, which has the undetermined position of the coordinate system and the nearly coincident image region with the image data with the determined position of the coordinate system, is present, the position determination means determines the position of the coordinate system of the image data, which has the undetermined position of the coordinate system, based on a mutual positional relation between the image data when the image data with the determined position of the coordinate system and the image data with the undetermined position of the coordinate system are arranged such that image regions nearly coinciding with each other overlap each other.

7. The information management system according to claim 6, wherein when it is determined whether the image regions nearly coinciding with each other is present between the image data, the overlap detection means extracts a position of a characteristic point of the image data in response to a type of an object photographed by the photographing means, compares an arrangement pattern of the characteristic point for each of the image data, and determines that image regions nearly coinciding with each other is present when a part in which the arrangement patterns of the characteristic points nearly coincide with each other is present.

8. The information management system according to claim 7, wherein the surface serving as the object to be photographed by the photographing means is a surface of a skin, and the characteristic point to be extracted from the image data by the overlap detection means is a predetermined part of each pore on the skin surface.

9. The information management system according to claim 7, wherein the surface serving as the object to be photographed by the photographing means is a surface of a skin, and the characteristic point to be extracted from the image data by the overlap detection means is a predetermined part of each spot of equal to or smaller than a predetermined size on the skin surface.

10. An information management method measurement and analysis of a surface condition, the method being performed by an information management system for measurement and analysis of the surface condition, the system being provided with a photographing means that photographs a surface serving as an object to be measured without fixing a photographing position and generates image data, and an image storage means that stores the image data and a photographing date of the image data, the method comprising:

comparing a plurality of the image data stored in the image storage means and determining relative positions of the plurality of image data in a single coordinate system when the plurality of image data, obtained from a plurality of times of photographing performed at an interval using the photographing means, of which photographing positions on the surface serving as the object to be photographed are deviated are stored in the image storage means, wherein a center of the respective image data of which the relative positions in the coordinate system are determined is arranged and displayed while deviating from the relative positions in the coordinate system in an order of the photographing date; and displaying the image data stored in the image storage means in the order of the photographing date of the image data.

11. The information management method according to claim 10, the method further comprising:

an image display step of displaying the image data stored in the image storage means in the order of the photographing date of the image data, wherein, in the image display step, the respective image data of which the coordinate system is set on a display screen and the positions in the coordinate system are determined is arranged at the positions of the coordinate system, and the image data is displayed in the order of the photographing date.

12. The information management method according to claim 11, wherein in the image display step, the image data is displayed on a frontmost surface in the order of the photographing date to be held in a state of displaying a part of the image data to be displayed on the frontmost surface, which is displayed prior to relevant image data, that does not overlap with the relevant image data to be displayed on the frontmost surface.

13. The information management method according to claim 11, wherein in the image display step, image data, interpolated from the image data having the preceding or subsequent photographing date, is generated at time of displaying the image data in the order of the photographing date when a display range to display relevant image data includes a part in which displayed relevant image data is present and a apart in which the relevant image data is absent, and the image data having the preceding or subsequent photographing date than the displayed relevant image data is present in the part in which the relevant image data is absent, and the interpolated image data is displayed in the part of the display range in which the displayed image data is absent.

14. The information management method according to claim 10, wherein in the position determination step, when a nearly coincident image region is present between the image data to be compared with each other, relative positions of the plurality of image data in the single coordinate system are determined based on the image region.

15. The information management method according to claim 14, further comprising:

comparing the image data sequentially stored in the image storage means, and determining whether the image regions nearly coinciding with each other are present in the image data, wherein the coordinate system having one of the image data is set as a reference when the image regions nearly coinciding with each other are present, and a position in the coordinate system of another image data in a state in which the image region the image region that nearly coincides with the one image is superposed is determined, the image data of which the position of the coordinate system is already determined by the position determination means, and the image data of which the position of the coordinate system is not yet determined are compared to determine whether the image regions nearly coinciding with each other is present, and when the image data, which has the undetermined position of the coordinate system and the nearly coincident image region with the image data with the determined position of the coordinate system, is present, the position of the coordinate system of the image data, which has the undetermined position of the coordinate system, is determined based on a mutual positional relation between the image data when the image data with the determined position of the coordinate system and the image data with the undetermined position of the coordinate system are arranged such that image regions nearly coinciding with each other overlap each other.

16. The information management method according to claim 15, wherein when it is determined whether the image regions nearly coinciding with each other is present between the image data, a position of a characteristic point of the image data is extracted in response to a type of an object photographed by the photographing means, an arrangement pattern of the characteristic point is compared for each of the image data, and it is determined that image regions nearly coinciding with each other is present when a part in which the arrangement patterns of the characteristic points nearly coincide with each other is present.

17. The information management method according to claim 16, wherein the surface serving as the object to be photographed by the photographing means is a surface of a skin, and the characteristic point to be extracted from the image data in the overlap detection step is a predetermined part of each pore on the skin surface.

18. The information management method according to claim 16, wherein the surface serving as the object to be photographed by the photographing means is a surface of a skin, and the characteristic point to be extracted from the image data in the overlap detection step is a predetermined part of each spot of equal to or smaller than a predetermined size on the skin surface.

* * * * *